(12) United States Patent
Kobayashi et al.

(10) Patent No.: US 7,011,667 B2
(45) Date of Patent: Mar. 14, 2006

(54) APPARATUS FOR LIGATING LIVING TISSUES

(75) Inventors: Tsukasa Kobayashi, Hachioji (JP); Junichi Muramatsu, Akiruno (JP); Takayuki Suzuki, Yokohama (JP); Ko Kimura, Yokohama (JP); Hideki Shimonaka, Hachioji (JP)

(73) Assignee: Olympus Corporation, Tokyo (JP)

( * ) Notice: Subject to any disclaimer, the term of this patent is extended or adjusted under 35 U.S.C. 154(b) by 214 days.

(21) Appl. No.: 10/091,894

(22) Filed: Mar. 6, 2002

(65) Prior Publication Data

US 2002/0128667 A1    Sep. 12, 2002

(30) Foreign Application Priority Data

Mar. 7, 2001    (JP) ............................ 2001-063931
Oct. 18, 2001   (JP) ............................ 2001-321002

(51) Int. Cl.
*A61B 17/10*    (2006.01)
(52) U.S. Cl. ...................... 606/142; 606/139; 606/143
(58) Field of Classification Search ................ 606/142, 606/139, 143, 151, 157, 158; 227/175.1
See application file for complete search history.

(56) References Cited

U.S. PATENT DOCUMENTS

| | | | | |
|---|---|---|---|---|
| 5,100,418 A | * | 3/1992 | Yoon et al. ................. | 606/139 |
| 5,174,276 A | * | 12/1992 | Crockard .................... | 600/104 |
| 5,207,692 A | * | 5/1993 | Kraus et al. ................ | 606/143 |
| 5,242,456 A | | 9/1993 | Nash et al. | |
| 5,833,700 A | * | 11/1998 | Fogelberg et al. .......... | 606/158 |
| 6,814,742 B1 | * | 11/2004 | Kimura et al. .............. | 606/151 |
| 6,923,818 B1 | * | 8/2005 | Muramatsu et al. ........ | 606/142 |

FOREIGN PATENT DOCUMENTS

| | | |
|---|---|---|
| DE | 26 04 024 | 8/1976 |
| DE | 102 03 956 A1 | 9/2002 |
| JP | 63-267345 | 11/1998 |

* cited by examiner

*Primary Examiner*—Anhtuan T. Nguyen
*Assistant Examiner*—Darwin P Erezo
(74) *Attorney, Agent, or Firm*—Scully, Scott, Murphy & Presser

(57) ABSTRACT

The present invention has an introducing tube capable of being inserted into a living body cavity, a manipulating wire movably inserted into this introducing tube, at least two or more clips, and a ligating wire causing the clip and the manipulating wire to be engaged with each other wherein, when the clip is ligated, a tensile stress of the manipulating wire is always applied only to the clip located at the most distal end.

3 Claims, 14 Drawing Sheets

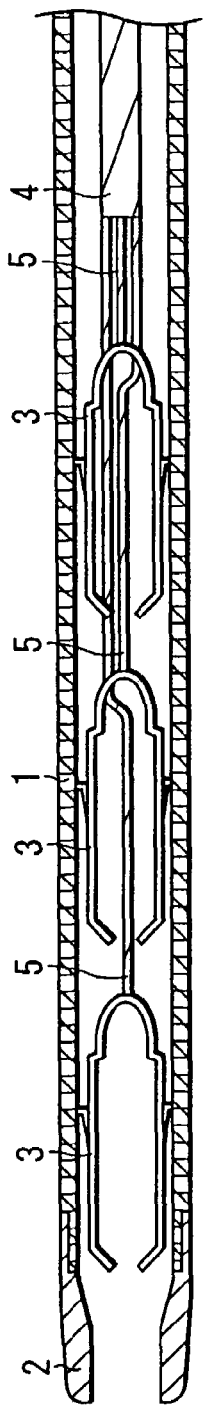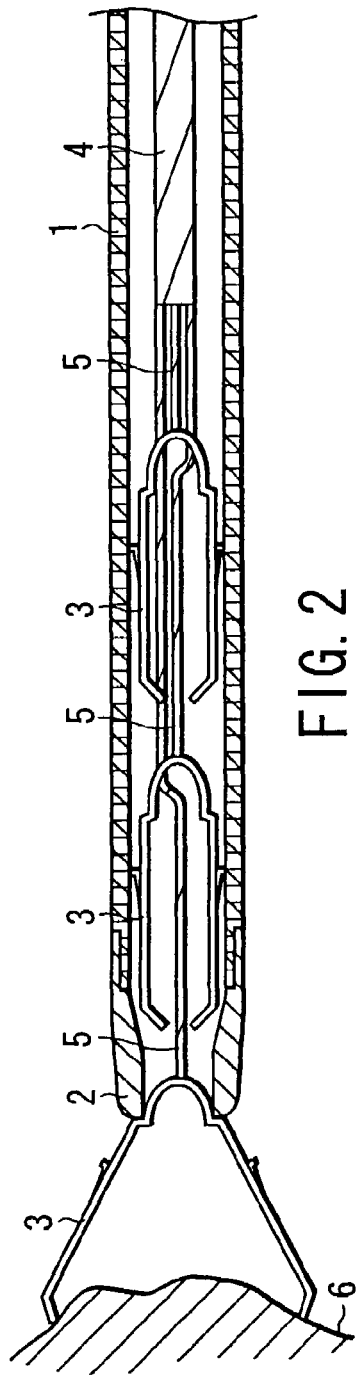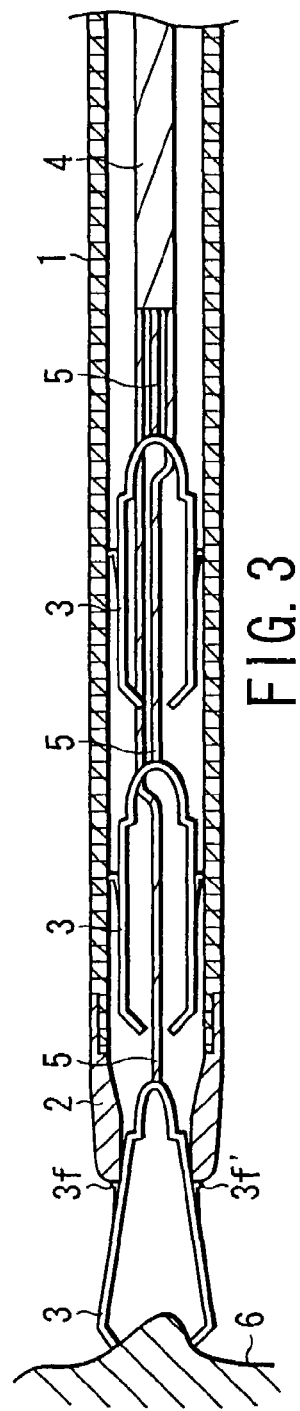

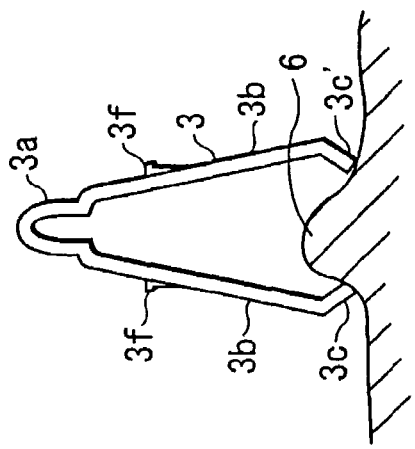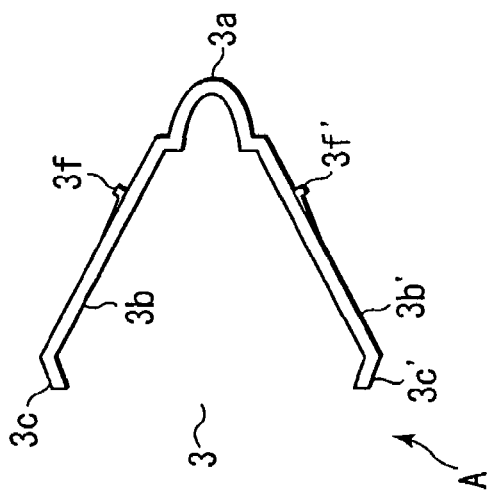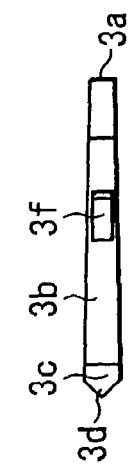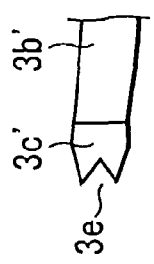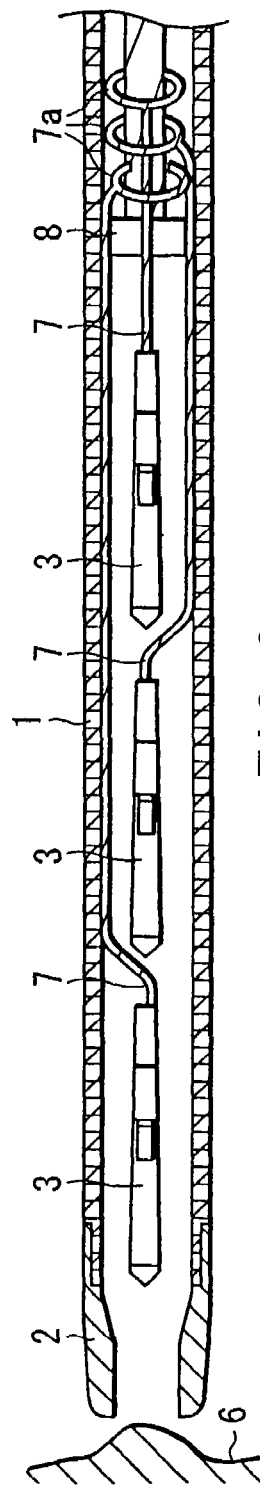

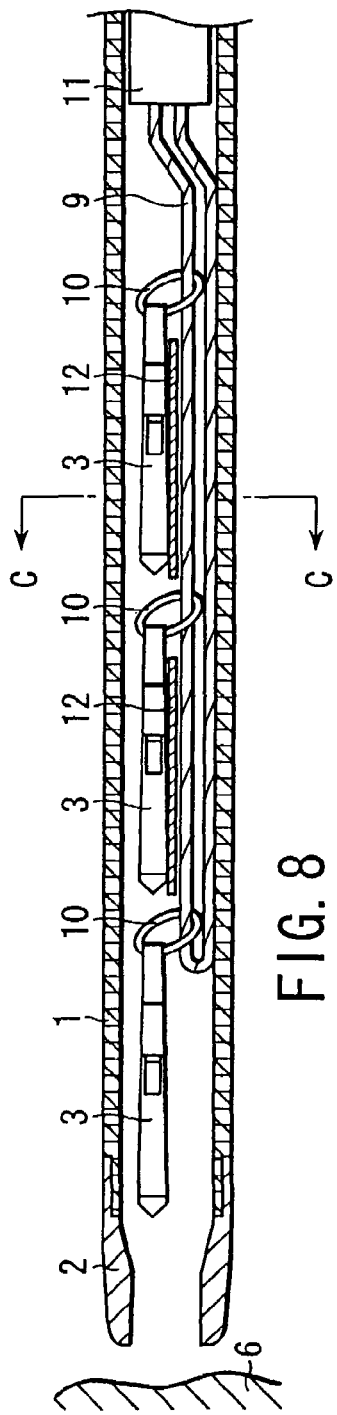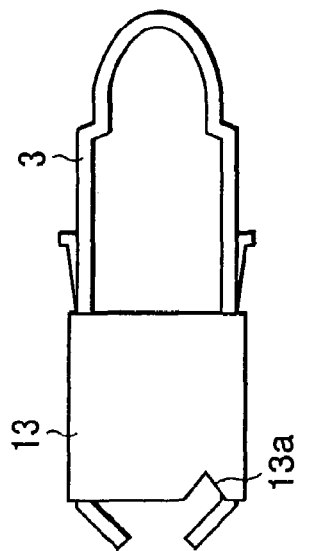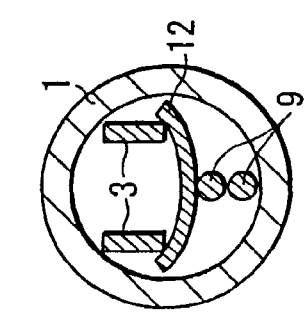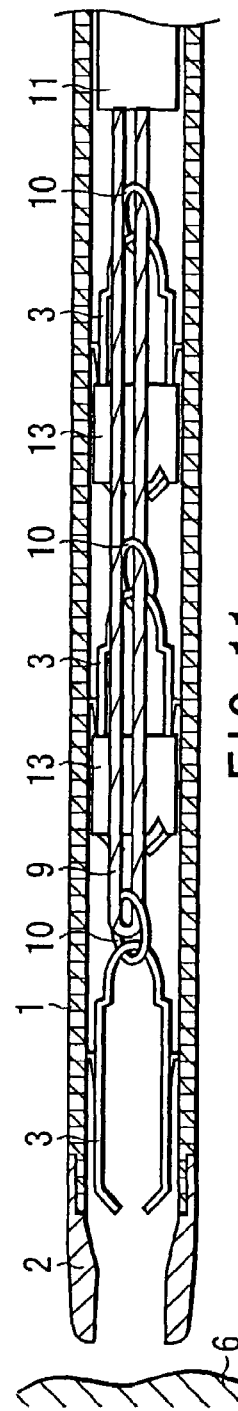
FIG. 8
FIG. 12
FIG. 10
FIG. 9
FIG. 11

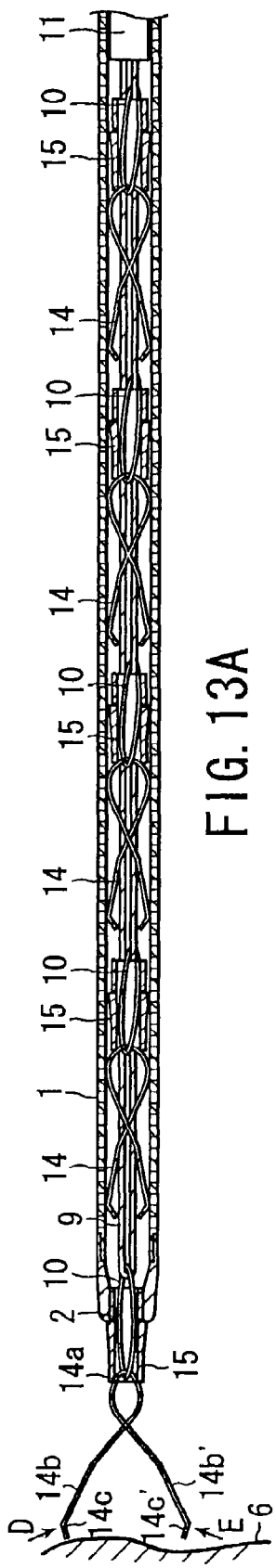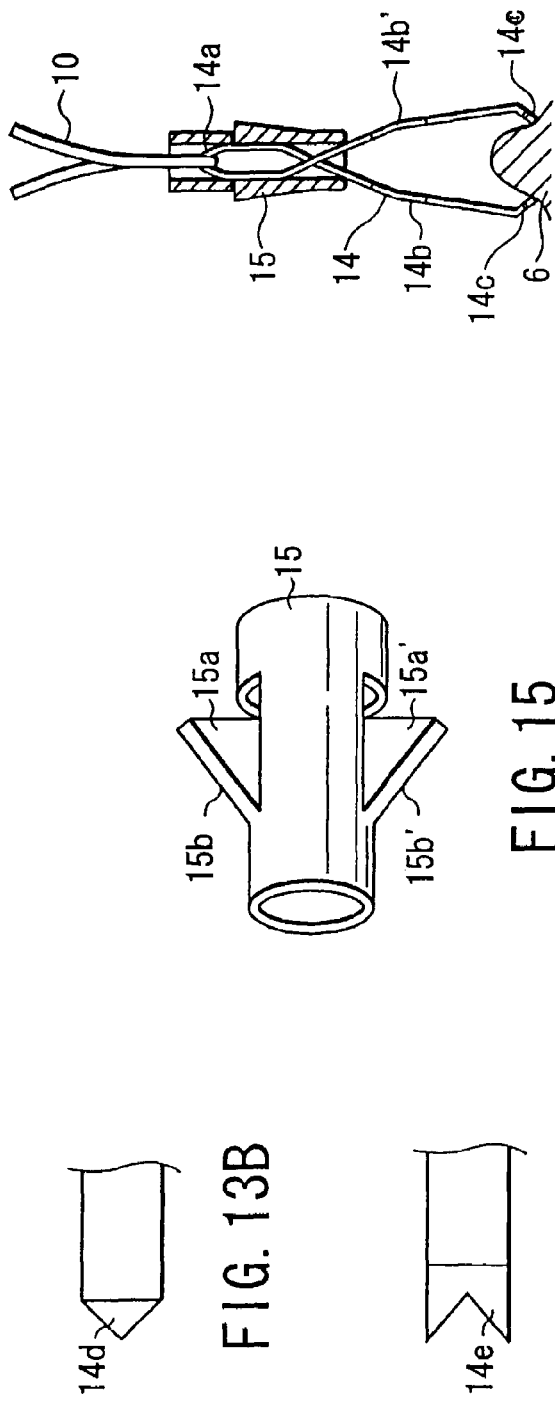

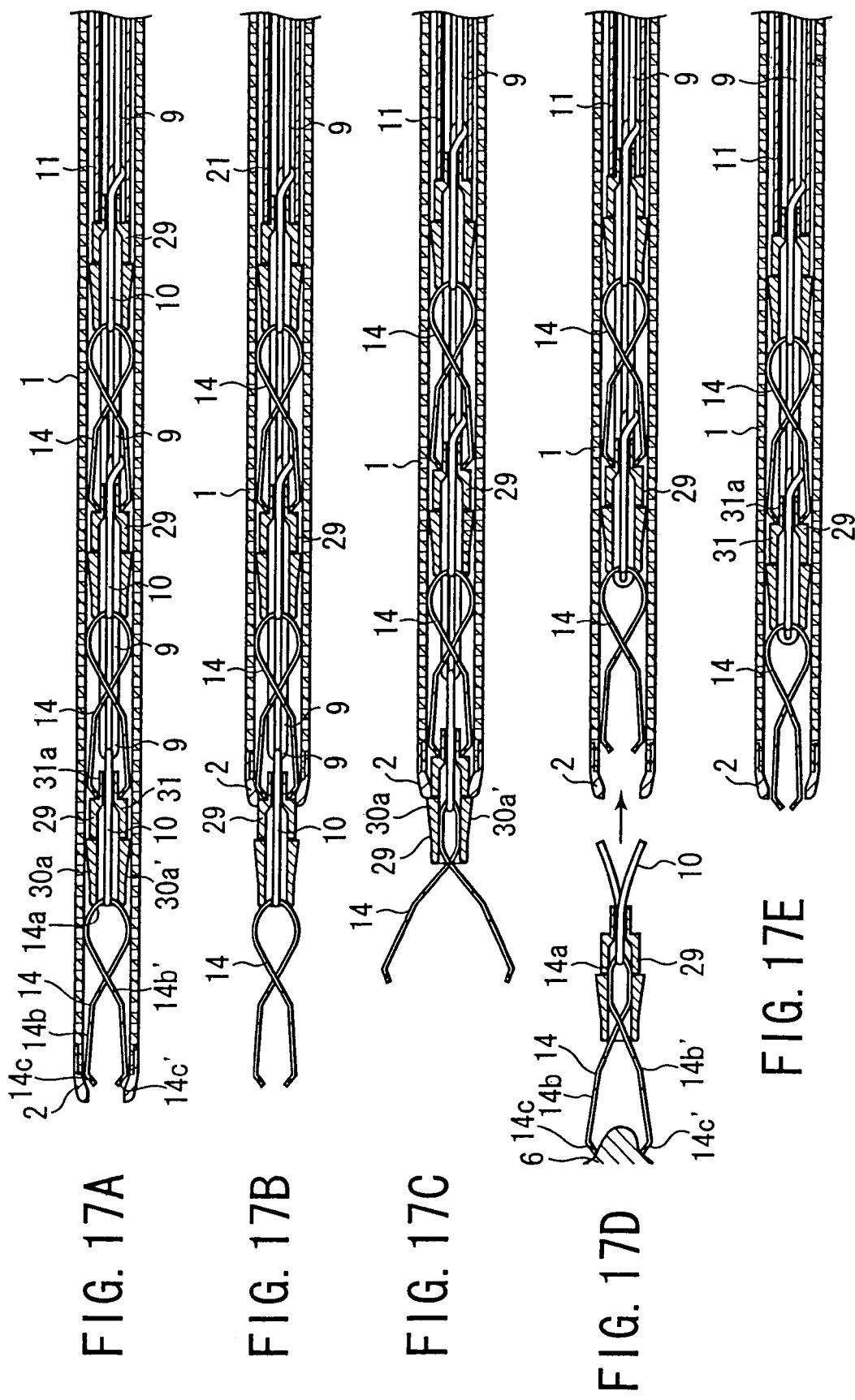

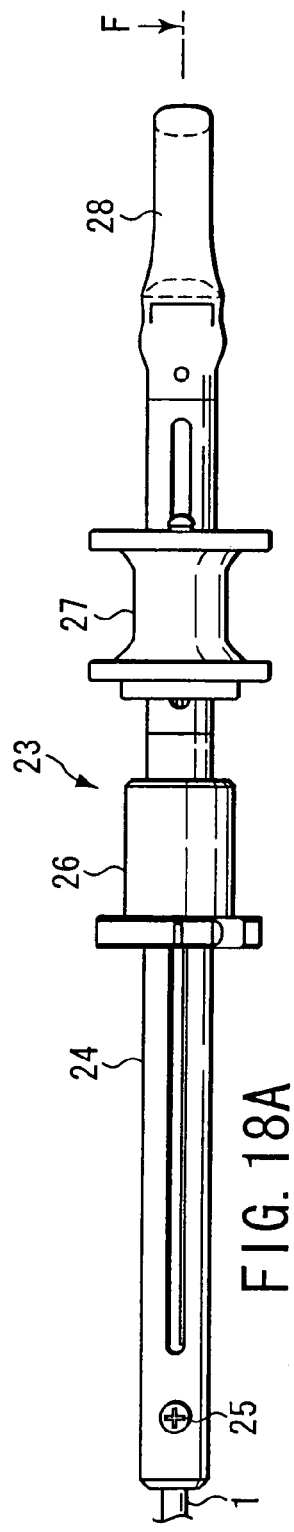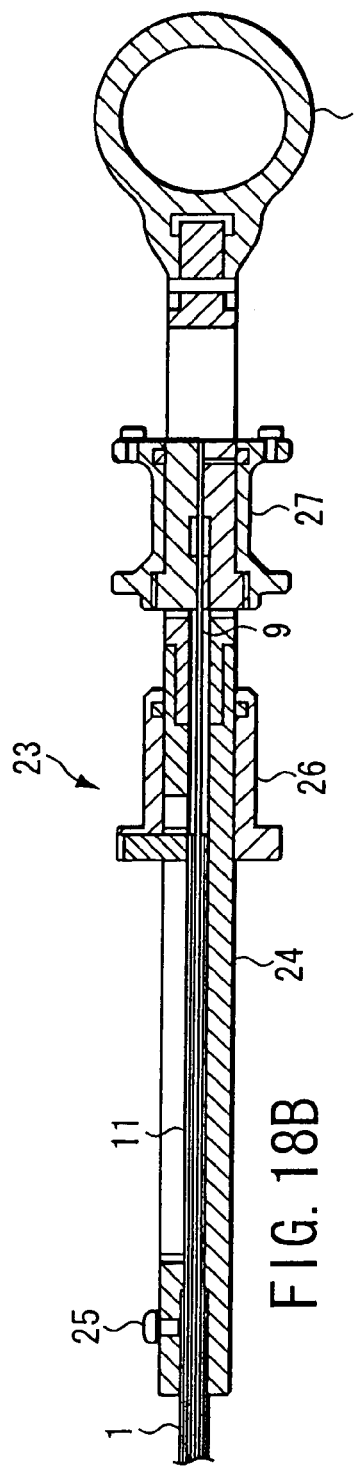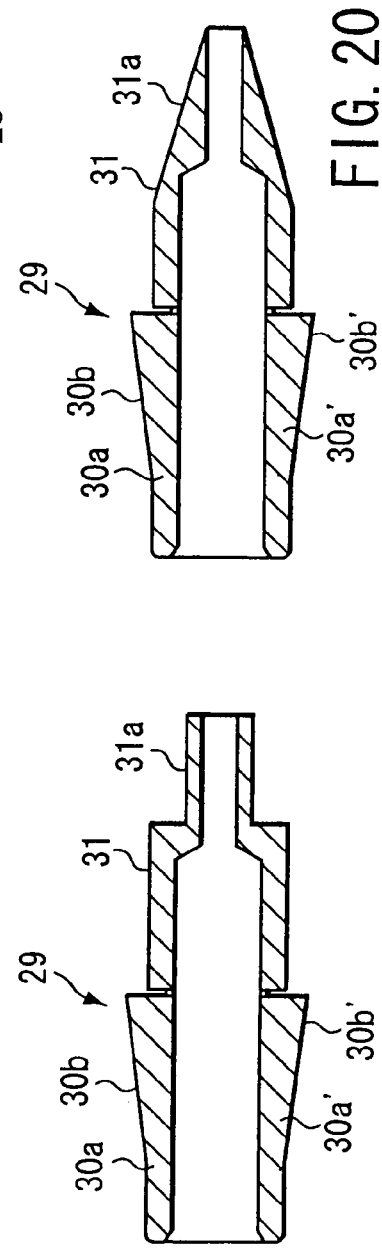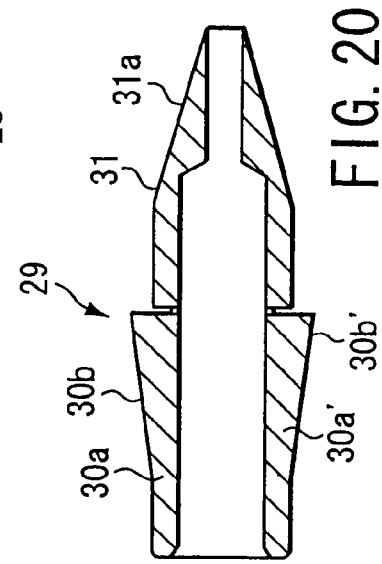
FIG. 18A
FIG. 18B
FIG. 19
FIG. 20

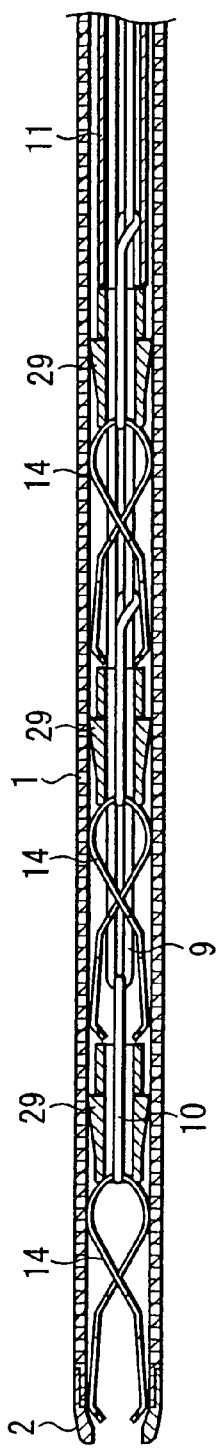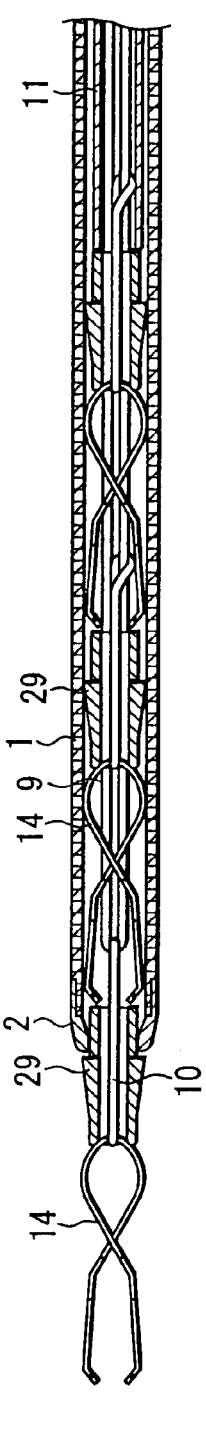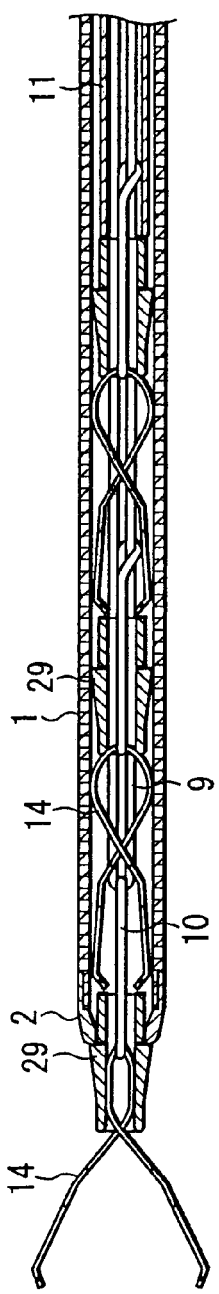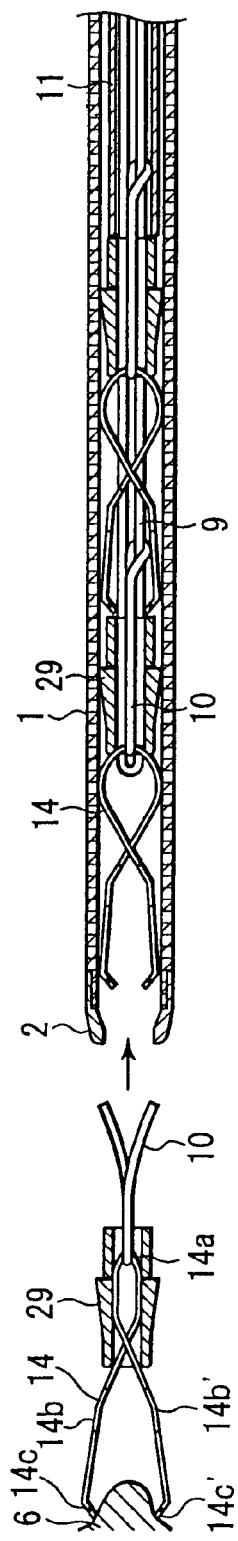
FIG. 21A
FIG. 21B
FIG. 21C
FIG. 21D

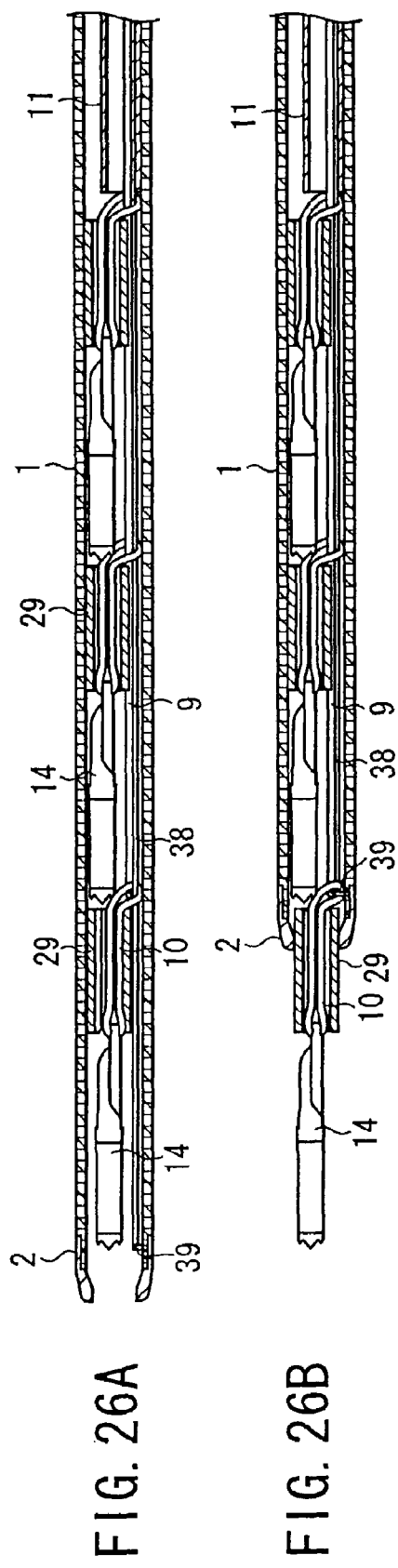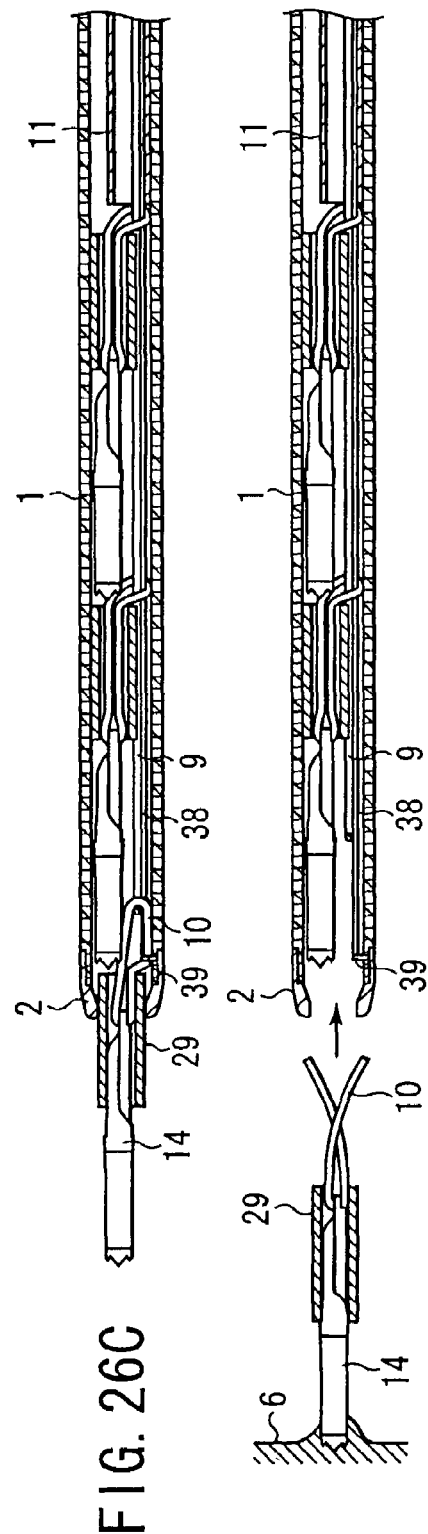
FIG. 26A
FIG. 26B
FIG. 26C
FIG. 26D

APPARATUS FOR LIGATING LIVING TISSUES

CROSS-REFERENCE TO RELATED APPLICATIONS

This application is based upon and claims the benefit of priority from the prior Japanese Patent Applications No. 2001-063931, filed Mar. 7, 2001; and No. 2001-321002, filed Oct. 18, 2001, the entire contents of both of which are incorporated herein by reference.

BACKGROUND OF THE INVENTION

1. Field of the Invention

The present invention relates to an apparatus for ligating living tissues for clipping a living tissue by inserting a clip into a living body cavity in a transendoscopic manner.

2. Description of the Relate Art

Conventionally, in Jpn. Pat. Appln. KOKAI Publication No. 63-267345, for example, it has been well known that a physiological tissue clipping apparatus incorporates a plurality of clips in an introducing tube, and carries out legation work continuously. There has been proposed a clipping apparatus in which a plurality of clips is incorporated in an introducing tube, each of these clips and a manipulating member are connected to each other with an aid of a substance having its low melting point, and the substance having its low melting point is fused while the clips are inserted in the cavity so as to continuously carry out a clip legation work.

However, this clipping apparatus disclosed in Jpn. Pat. Appln. KOKAI Publication No. 63-267345 requires heating means for generating a heat during clip opening and during clip legation. Thus, there has been a problem that clip legation requires a complicated work and much time. In addition, in carrying out legation while a clip is protruded from an introducing tube, when the clip is protruded, one must manipulate the apparatus while observing an endoscopic image. In addition, careful protrusion work is required at the front side of the clipping apparatus, and a plurality of clips may be protruded from a distal end of the introducing tube at one breath.

BRIEF SUMMARY OF THE INVENTION

The present invention has been made in order to solve the foregoing problem. It is an object of the present invention to provide an apparatus for ligating living tissues capable of speedily and easily continuing a clip legation work merely by extruding or retracting a manipulating wire while a plurality of clips are mounted in the introducing tube and are inserted into the cavity.

It is another object of the present invention to provide an apparatus for ligating living tissues capable of providing a mechanism for preventing any object other than clips mounted at the most distal end from being protruded from an introducing tube, thereby eliminating a careful work at its frontal side; enabling simplification of manipulation, enabling reduction of a surgical operation time when carrying out continuous legation, and enabling reduction of burdens of a patient and a surgeon.

According to the present invention, there can be provided an apparatus for ligating living tissues comprising:

an introducing tube capable of being inserted into a living tissue;

a manipulating wire movably inserted into the introducing tube;

at least two or more clips housed in the introducing tube; and a connection structure for engaging the clips and the manipulating wire with each other, wherein, in ligating the clips, a tensile stress of the manipulating wire is always applied only to the clip located at the most distal end.

Therefore, in ligating clips, the tensile stress of the manipulating wire is always applied to the clip at the distal end, whereby, while a plurality of clips are mounted in the introducing tube, and are inserted into the body cavity, a clip legation work can be continuously carried out speedily and easily merely by extruding/retracting the manipulating wire.

In addition, according to the present invention, there can be provided an apparatus for ligating living tissues comprising:

an introducing tube capable of being inserted into a living body cavity;

a manipulating wire movably inserted into the introducing tube; and at least two or more clips each having a proximal end portion and having an opening/expanding property in which a pinch portion is formed at a distal end of an arm section that extends from this proximal end portion, wherein two or more clips are disposed in series in the introducing tube, and, in protruding the clips from the introducing tube, a mechanism for preventing any object other than the clip mounted at the most distal end from being protruded from the introducing tube.

Therefore, any object other than the clip mounted at the most distal end can be prevented from being protruded from the introducing tube, and a careful work at its frontal side is eliminated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiment of the invention, and together with the general description given above and the detailed description of the embodiment given below, serve to explain the principles of the invention.

FIG. 1 is a longitudinal side section showing a distal end portion of a clipping apparatus according to a first embodiment of the present invention;

FIG. 2 is a longitudinal side section showing a distal end portion of the clipping apparatus according to the present embodiment;

FIG. 3 is a longitudinal side section showing a distal end portion of the clipping apparatus according to the present embodiment;

FIG. 4A is a plan view showing a clip according to the present embodiment;

FIG. 4B is a plan view showing a clip according to the present embodiment;

FIG. 4C is a view when the clip of the present embodiment is seen in a direction indicated by the arrow A in FIG. 4B;

FIG. 5 is a side view showing a state in which a target tissue is clipped by a clip according to the present embodiment;

FIG. 6 is a longitudinal side section showing a distal end portion of a clipping apparatus according to a second embodiment of the present invention;

FIG. 8 is a longitudinal side section showing a distal end portion of a clipping apparatus according to a fourth embodiment of the present invention;

FIG. 9 is a perspective view showing a partition member according to the present embodiment;

FIG. 10 is a sectional view taken along the line C—C in FIG. 8 according to the present embodiment;

FIG. 11 is a longitudinal side section showing a distal end portion of a clipping apparatus according to a fifth embodiment of the present invention;

FIG. 12 is a side view showing a restricting member according to the present embodiment;

FIG. 13A is a longitudinal side section showing a distal end portion of a clipping apparatus according to a sixth embodiment of the present invention;

FIG. 13B is a view seen in a direction indicated by the arrow D in FIG. 13A;

FIG. 13C is a view seen in a direction indicated by the arrow E in FIG. 13A;

FIG. 14 is a side view showing a state in which a target tissue is clipped by a clip according to the present embodiment;

FIG. 15 is a perspective view showing a clip tightening ring according to the present embodiment;

FIG. 17A to FIG. 17E are longitudinal side sections each showing a distal end portion of a clipping apparatus for explaining working of an eighth embodiment according to the present invention;

FIG. 18A is a side view showing a manipulating section according to the present embodiment;

FIG. 18B is a sectional view taken along the line F—F in FIG. 18A according to the present embodiment;

FIG. 19 is a longitudinal side section showing a clip tightening ring according to the present embodiment;

FIG. 20 is a longitudinal side section showing a modified example of the clip tightening ring according to the present embodiment;

FIG. 21A to FIG. 21D are longitudinal side sections each showing a distal end portion of a clipping apparatus for explaining working of a ninth embodiment according to the present invention;

FIG. 26A to FIG. 26D are longitudinal side sections each showing a distal end portion of a clipping apparatus for explaining working of a fourteenth embodiment according to the present invention.

DETAILED DESCRIPTION OF THE INVENTION

Figure 7A:
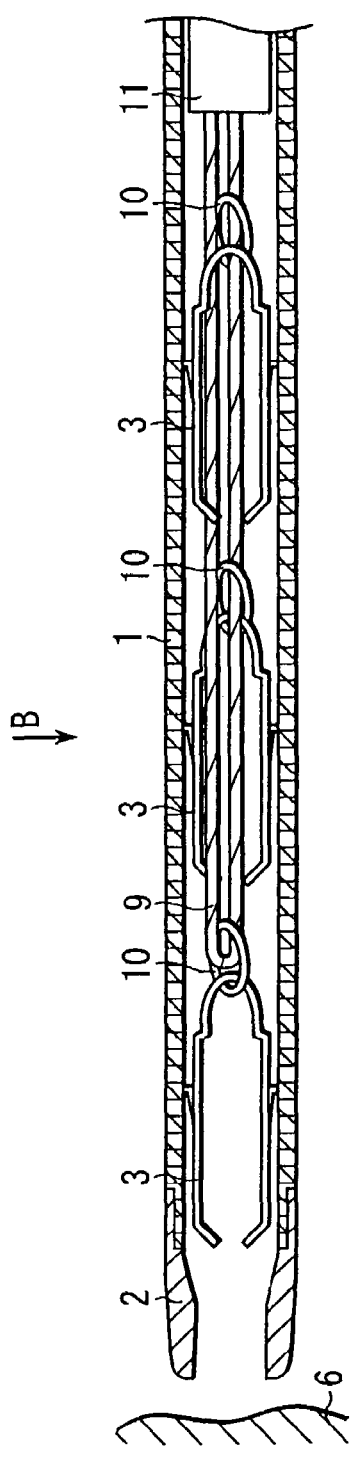
FIG. 7A is a longitudinal side section showing a distal end portion of a clipping apparatus according to a third embodiment of the present invention.
Figure 7B:
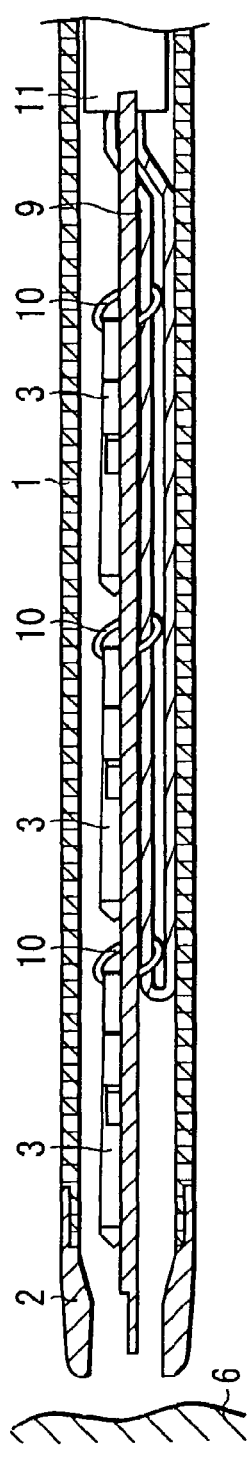
FIG. 7B is a longitudinal side section seen in a direction indicated by the arrow B in FIG. 7A.

Hereinafter, preferred embodiments of the present invention will be described with reference to the accompanying drawings.

FIG. 1 to FIG. 5 each show a first embodiment. FIG. 1 to FIG. 3 are longitudinal side sections each showing a distal end portion in an apparatus for ligating living tissues. An introducing tube 1 has flexibility such that the tube can be inserted into a channel of an endoscope. A distal end tip 2 is provided at a distal end portion of this introducing tube 1. This distal end tip 2 is fixed at the distal end portion of the introducing tube 1 by means of fusion welding, adhesive, or press-fit and the like. A manipulating wire 4 is movably inserted into the introducing tube 1. At the distal end portion of this manipulating wire 4, a clip 3 is fixedly mounted via a ligating wire 5.

The introducing tube 1 is provided as a coil sheath which has irregular internal and external faces on which a metallic wire (such as a stainless wire) whose section is round is closely wound. Thus, this introducing tube is structured so that the sheath does not break even if a force of compressing the sheath is applied to the distal and proximal end portions of the sheath.

In addition, the introducing tube 1 may be a coil sheath such that its flat internal and external faces are closely wound by a metallic wire after the metallic wire (such as a stainless wire) having its sectional round face has been crushed, and then, the sectional face of the wire has been formed in a rectangular shape. In this case, the flat internal face makes it easy to protrude the clip 3 and insert the manipulating wire 4. In addition, even if the element wire diameter of the same wire is used, a coil sheath with its large inner diameter can be provided as compared with a round shaped coil sheath. This makes it much easier to protrude the clip 3 and insert the manipulating wire 4.

Further, the introducing tube 1 may be a polymeric resin based tube sheath (such as synthetic polymeric polyamide, high density/low density polyethylene, polyester, polytetrafluoro ethylene, tetrafuoro ethylene-perfluoroalkylvinyl ether copolymer, or tetrafluoro ethylene-hexafluoro propylene copolymer). In this case, the internal and external faces of the sheath have slipping properties, thus making it easy to insert/remove the tube into/from the endoscope channel, protrude the clip 3, and insert the manipulating wire 4.

In addition, the introducing tube 1 may be a double tube having an inner layer and an outer layer at a wall section and may be a tube sheath embedded while a reinforce member is interposed between the double tubes.

In this case, the inner layer and outer layer are formed of the polymeric resin. The reinforce member is formed of a cylindrical blade or the like knitted with thin metal wires in a lattice shape. In this manner, even when a force of compressing the sheath is applied to the distal end portion and proximal end portion of the sheath, the sheath does not break because of its excellent compression resistance, as compared with a tube sheath in which no reinforce member is embedded.

The dimensions of the introducing tube 1 are defined as an outer diameter capable of being inserted into the endoscope channel. The thickness of the sheath is determined depending on rigidity of the element. When the introducing tube 1 is provided as a metallic sheath, the thickness is about 0.2 mm to 0.5 mm. In a tube made of a polymeric resin, the thickness is about 0.3 mm to 0.6 mm. There is an advantage that the reinforce member is embedded, thereby reducing the thickness and increasing the inner diameter of the sheath.

The distal end tip 2 is provided as a metallic short tube (such as a stainless tube), its outer periphery face is formed in a tapered shape, and its distal end portion is converged. This makes it easy to insert the introducing tube 1 into the endoscope channel. In addition, its inter periphery face is formed in a tapered shape as well, so that the clip 3 can be easily protruded from the distal end tip 2.

In addition, as shown in FIG. 4A to FIG. 4C, the inner diameter of the distal end portion of the distal end tip 2 is dimensionally set so that projections 3f and 3f' provided at arm sections 3b and 3b' of the clip 3 described later are engaged therewith, and the arm sections 3b and 3b' of the clip 3 can be opened. The outer diameter of the most distal end of this distal end tip 3 is 1.5 mm to 3.3 mm in diameter, and the inner diameter of the most distal end of the distal end tip 3 is about 1.0 mm to 2.2 mm in diameter.

At the clip 3, a metallic thin band plate is bent at its center portion, and such a bent portion is provided as a proximal end portion 3a. The arm sections 3b and 3b', both of which extend from this proximal end portion 3a, are bent in an expanding/opening direction. Further, the distal end rim portions of the arm sections 3b and 3b' each are bend so as to face to each other, and the bent sections are defined as pinch sections 3c and 3c'. One of the distal ends of the pinch sections 3c and 3c' is formed in a protrusive shape 3d, and the other is formed in a recess shape 3e so as to easily pinch a living tissue 6 (refer to FIG. 3). Then, opening/expanding properties are imparted to the arm sections 3b and 3b' so as to open the pinch sections 3c and 3c'.

Protrusions 3f and 3f' capable of being engaged with the distal end tip 2 (when a clip proximal end 3a is retracted into the distal end tip 2) are provided at the arm sections 3b and 3b' when the clip 3 is ligated. As a material for a thin band plate of the clip 3, there is used a stainless having its resilience or an ultra-elastic alloy such as a stainless or nickel-titanium alloy.

The manipulating wire 4 is about 0.3 mm to 1.5 mm in outer diameter. This wire is provided as a twisted wire made of stainless. This twisted wire is more flexible than a single wire. Thus, the flexibility of the introducing tube 1 itself is not degraded.

In addition, the manipulating wire 4 is connected to the clip 3 via the ligating wire 5. The proximal end side of this ligating wire 5 is welded or bonded with a distal end portion of the manipulating wire 4 by adhesive. In addition, the distal end side of the ligating wire 5 is bonded with the clip proximal end portion 3a by welding, adhesive, or alternatively, by forming a loop, and then, routing it into a bent portion of the clip 3. Further, the ligating wire undergoes extruding/retracting movement together with the clip 3 in accordance with extruding/retracting movement of the manipulating wire 4.

The ligating wire 5 is provided as a stainless based twisted wire or a single wire, for example. The outer diameter of the ligating wire 5 is 0.3 mm or less in diameter. Thus, it is required to define dimensions such that the ligating wire 5 breaks after a force of 1 to 5 Kg is applied during clip legation.

Now, working of a first embodiment will be described here.

The introducing tube 1 of the clipping apparatus is introduced into a body cavity via the channel of the endoscope inserted into the cavity. Then, the distal end portion of the introducing tube 1 is located at the target tissue 6, for example, in close proximity to a gastric mucous membrane tissue. The manipulating wire 4 is extruded in the distal end direction of the introducing tube 1, thereby protruding the first clip 3 located at the most distal end connected to the ligating wire 5 from the distal end portion of a distal end tip 2.

At the clip 3, opening/expanding properties are imparted to the arm sections 3b and 3b' so as to open the pinch sections 3c and 3c'. Thus, the clip 3 is protruded from the distal end tip 2, and at the same time, the pinch sections 3c and 3c' open. While the pinch sections 3c and 3c' are pushed against the target tissue 6, the manipulating wire 4 is retracted. The clip arm sections 3b and 3b' bend in the expanding/opening direction are engaged with the distal end portion of the distal end tip 2.

When the manipulating wire 4 is further retracted, the projections 3f and 3f' provided at the clip arm sections 3b and 3b' are engaged with the distal end tip 2, and the traction force is applied only to the clip 3. Therefore, as shown in FIG. 5, the proximal end portion 3a of the clip 3 is plastically deformed, and the pinch sections 3c and 3c' close, whereby the target tissue 6 can be pinched.

Further, the manipulating wire 4 is retracted, and the traction force is applied to the ligating wire 5 bonded with the proximal end portion 3a of the clip 3. Then, the ligating wire 5 itself connected to the clip 3 breaks, and the manipulating wire 4 and clip 3 are completely separated from each other. In this manner, legation of the first clip 3 located at the most distal end completes. The second or later clip 3 can be ligated in the same manner as in the first clip.

According to the first embodiment, the respective clip and manipulating wire are bonded with each other by means of the ligating wire, whereby a clip legation work can be continuously carried out speedily and easily merely by extruding/retracting the manipulating wire. This makes it possible to reduce a surgical operation time and to reduce burdens of the patient and surgeon.

FIG. 6 is a longitudinal side view showing a distal end portion of a clipping apparatus according to a second embodiment. Like constituent elements in the first embodiment are designated by like reference numerals. A duplicate description is omitted here. A loop shape 7a is formed at the proximal end side of the ligating wire 7 connecting the manipulating wire 4 and clip 3 with each other, and the loop 7a is routed into the manipulating wire 4. In addition, the distal end side of the ligating wire 7 is welded and bonded with the proximal end portion 3a of the clip 3, or alternatively, is bonded by forming the loop 7a, and then, mounting the loop on the proximal end portion 3a of the clip 3. Further, the ligating wire can freely move on the operating wire 4 without following the extruding/retracting movement of the manipulating wire 4.

This ligating wire 7 is provided as a metallic twisted wire or a single metallic wire, and is made of a polymeric fiber such as polyparaphenylenebenzo bis oxazol, polyethylene, or a liquid crystal polymer.

In addition, the outer diameter of the ligating wire 7 is 0.3 mm or less in diameter. In addition, it is required to set the outer diameter to dimensions such that the ligating wire 7 breaks when a force of 1 to 5 Kg is applied during legation of the clip 3.

Further, a stopper 8 is provided at the proximal end portion of the ligating wire 7. This stopper 8 can be inserted into the introducing tube 1, and is bonded with the distal end portion of the manipulating wire 4 by welding or adhesive. The stopper 8 is made of stainless or rubber and the like, for example, and has its size such that the loop 7a at the proximal end side of the ligating wire 7 does not slip off from the manipulating wire 4.

Now, working of a second embodiment will be described here.

The introducing tube 1 of the clipping apparatus is introduced into the body cavity via the channel of the endoscope inserted into the cavity. The distal end portion of the introducing tube 1 is located at the target tissue 6, for example, in close proximity to the gastric mucous membrane tissue. The manipulating wire 4 is extruded in the distal end direction of the introducing tube 1, whereby the proximal end portion 3a of the clip 3 located at the most distal end is extruded by means of the stopper 8. Then, a force is conveyed from the distal end portion of the clip 3 to the clip 3 at the distal end side, and the first clip 3 located at the most distal end is protruded from the distal end portion of the distal end tip 2.

At the clip 3, the opening/expanding properties are imparted to the arm sections 3b and 3b' so as to open the pinch sections 3c and 3C'. Thus, the clip 3 is protruded from the distal end tip 2, and at the same time, the pinch sections 3c and 3c' open. When the manipulating wire 4 is retracted while the pinch sections 3c and 3c' are pushed against the target tissue 6, the ligating wire 7 can freely move on the manipulating wire 4. Thus, the loop 7a of the ligating wire 7 on the manipulating wire 4 is hooked by the stopper 8, the clip 3 located at the most distal end is retracted, and the clip arm sections 3b and 3b' bent in the expanding/opening direction are engaged with the distal end portion of the distal end tip 2.

Further, when the manipulating wire 4 is retracted, the projections 3f and 3f' provided at the clip arm sections 3b and 3b' is engaged with the distal end tip 2, and the traction force is applied onto to the clip 3. Then, the proximal end portion 3a of the clip 3 is plastically deformed, and the pinch sections 3c and 3c' close, whereby the target tissue 6 can be pinched. Further, when the manipulating wire 4 is retracted, a portion of connection with the clip 3 of the ligating wire 7 breaks, and the manipulating wire 4 and clip 3 are completely separated from each other. In this manner, legation of the first clip 3 located at the most distal end completes. The second or later clip can be ligated in the same manner as in the first clip.

According to the second embodiment, the manufacturing cost can be reduced as compared with the first embodiment because no connection between the manipulating wire and ligating wire is made. In addition, the hardening of the manipulating wire due to welding or adhesive of the ligating wire is prevented, making it possible to reduce the traction force quantity and extrusion force quantity of the manipulating wire when an endoscope angle changes.

FIG. 7A to FIG. 7D each show a third embodiment. Like constituent elements in the first embodiment are designated by like reference numerals. A duplicate description is omitted here.

The manipulating wire 9 movably inserted into the introducing tube 1 returns one wire at the distal end of the introducing tube 1, and is formed as two wires at the proximal end of the introducing tube 1. This manipulating wire 9 is provided as a twisted metallic wire or a single metallic wire, for example, and is made of a polymeric fiber such as polyparaphenylenebenzo bis oxazol, polyethylene, or a liquid crystal polymer, and the outer diameter is about 0.3 mm to 1.0 mm. The manipulating wire 9 may be coated with a polymeric resin with its high slipping properties such as high density/low density polyethylene or polytetrafluoro ethylene, for example. The thickness of the coat is optimally about 0.05 mm to 0.1 mm. Further, in order to increase the slipping properties of the manipulating wire 9, it is effective to apply emboss processing of 0.01 mm to 0.45 mm onto the surface of the wire or to apply silicone coil thereto.

The clip 3 is connected to the manipulating wire 9 via the ligating wire 10. This ligating wire 10 is formed in a loop shape. This loop is routed through the manipulating wire 9 and the proximal end portion 3a of the clip 3, whereby the manipulating wire 9 and clip 3 are connected with each other. Further, the ligating wire can freely move on the manipulating wire 9 irrespective of the extruding/retracting movement of the manipulating wire 9.

The ligating wire 10 is provided as a twisted metallic wire or a single metallic wire, and is made of a polymeric fiber such as polyparaphenylene benzo bis oxazol or polyethylene. Preferably, polyamide which easily slips on the manipulating wire 9 is desirable.

Further, the outer diameter of the ligating wire 10 is about 0.15 mm to 0.6 mm in diameter. In addition, it is required to set the dimensions such that the ligating wire 10 breaks when a force of 1 to 5 Kg is applied during legation of the clip 3. In addition, the loop diameter of the ligating wire 10 is 5 mm to 20 mm in diameter. This diameter is defined as a sufficient length such that the clip 3 does not move in accordance with the extruding/retracting movement of the manipulating wire 9.

Figure 7C:
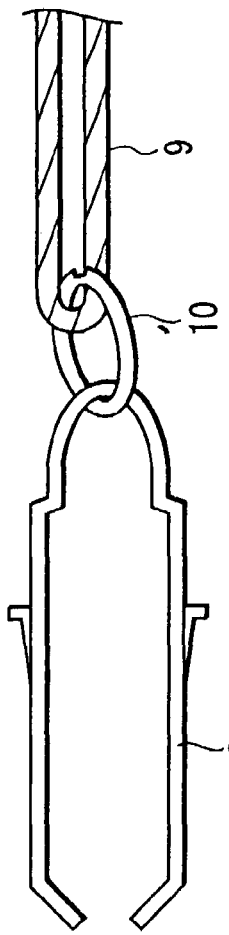
FIG. 7C is a side view showing a modified example of a ligating wire.

In addition, when the ligating wire 10 breaks, thereby carrying out clip legation, if the ligating wire 10 is fully introduced into the introducing tube 1 at the clip side, when the second or later clip 3 is protruded, the clip 3 and ligating wire 10 is sandwiched between the distal end tips 2. As a result, the clip 3 may not be protruded. Therefore, the ligating wire 10 and clip 3 are bonded or fused with each other. Alternatively, as shown in FIG. 7C, it is desirable that a cutout be provided at a portion abutting against the manipulating wire 9, the ligating wire 10 be always broken at the manipulating wire 9, and the ligating wire 10 be attached to the clip 3 after ligated.

The proximal end of the manipulating wire 9 is inserted into a compression member 11. This compression member 11 has its flexibility such that the compression member can be inserted into the introducing tube 1. In this way, the clip 3 mounted in the introducing tube 1 is protruded from the distal end portion of the distal end tip 2.

This compression member 11 is provided as a coil sheath having irregularities on its internal and external faces on which a sectional round shaped metallic wire (such as a stainless wire) is closely wound. The compression member 11 is moved to the distal end side relevant to the introducing tube 1, thereby making it possible to extrude the clip 3 from the introducing tube 1.

The compression member 11 may be provided a rectangular coil sheath having its flat internal and external faces, the coil being closely wound after a sectional round shaped metallic wire (such as a stainless wire) has been crushed, thereby making the sectional wire face rectangular. Even if the element wire diameter of the same wire is used, a coil sheath with its large inner diameter dimensions can be achieved as compared with the round shaped coil sheath. This makes it easier to protrude the clip 3 and insert the manipulating wire 9.

The compression member 11 is provided as a tube sheath made of a polymeric resin (such as synthetic polymeric polyamide, high density/low density polyethylene, polyester, polyterafluoro ethylene, tetrafluoro ethylene-perfluoroalkylvinyl ether copolymer, tetrafluoro ethylene-hexafluoro propylene copolymer). This member has its slipping properties on the internal and external faces of the sheath, thus facilitating insertion in the introducing tube 1 and insertion of the manipulating wire 9.

Figure 7D:
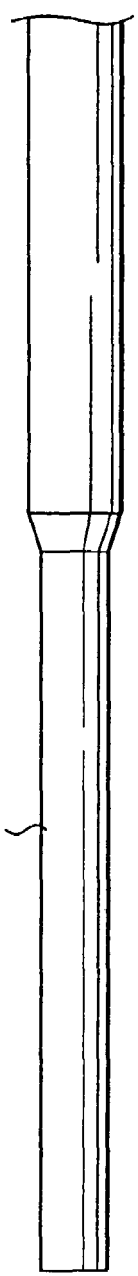
FIG. 7D is a side view showing a modified example of a compression member.

Further, the compression member 11 has its outer diameter such that the compression member can be inserted into the introducing tube 1 and its inner diameter such that the manipulating wire 9 can be inserted. The outer diameter is 3 mm or less in diameter, and the inner diameter is maximally large. However, the required thickness is such that the compression member does not break even if a force is applied when the clip 3 is extruded. In addition, as shown in FIG. 7D, it is desirable that the compression member 11 is small in outer diameter at its distal end side, and is large in outer diameter at its frontal side.

Now, working of a third embodiment will be described here.

The introducing tube 1 of the clipping apparatus is introduced into the body cavity via the channel of the endoscope inserted into the cavity. Then the distal end portion of the introducing tube 1 is located at the target tissue 6, for example, the proximity of the gastric mucous membrane tissue. The compression member 11 is extruded in the distal end direction of the introducing tube 1, whereby the proximal end portion 3a of the clip 3 located at the most proximal end is compressed by the compression member 11. Then, a force is conveyed from the distal end portion of the clip 3 to the clip 3 at the distal end side, and the first clip 3 located at the most distal end is protruded from the distal end portion of the distal end tip 2.

At the clip 3, the opening/expanding properties are imparted to the arm sections 3b and 3b' so as to open the pinch sections 3c and 3c'. Thus, the clip 3 is protruded from the distal end tip 2, and at the same time, the pinch sections 3c and 3c' open. While the pinch sections 3c and 3c' are pushed against the target tissue 6, when two manipulating wires 9 exposed from the proximal end of the introducing tube 1 are retracted, the legation wire 10 freely moves on the manipulating wire 9. Thus, a loop of the legation wire 10 is hooked on a return portion of the manipulating wire 9 at the distal end of the introducing tube 1, the clip 3 at the most distal end is retracted, and the clip arm sections 3b and 3b' bent in the expanding/opening direction are engaged with the distal end portion of the distal end tip 2.

When the manipulating wire 9 is further retracted, the projections 3f and 3f' provided at the clip arm sections 3b and 3b' are engaged with the distal end tip 2. Then, the traction force is applied onto to the clip 3, the proximal end portion 3a of the clip 3 is plastically deformed, and the pinch sections 3c and 3c' are closed, whereby the target tissue 6 can be pinched.

When the manipulating wire 9 is further retracted, the ligating wire 10 breaks, and the manipulating wire 9 and clip 3 are completely separated from each other. In this manner, ligation of the first clip 3 located at the most distal end completes. At this time, a legation wire 10 other than that engaged with the clip 3 located at the most distal end has its sufficient length. Thus, this wire does not follow retraction of the manipulating wire 9 and does not move. The second or later clip can be ligated in the same manner as in the first clip.

According to the third embodiment, the ligating wire can be easily constructed as compared with the first and second embodiments because the ligating wire is routed through the manipulating wire and the clip bent portion during construction, thereby making it possible to reducing the manufacturing cost. In addition, a clip other than that located at the most distal end does not move when the manipulating wire is retracted during clip legation, thus making it possible to reduce the retraction force quantity of the manipulating wire.

FIG. 8 to FIG. 10 each show a fourth embodiment. Like constituent elements in the third embodiment are designated by like reference numerals. A duplicate description is omitted here.

In order to prevent a hitch between the clip arm sections 3a and 3b' and manipulating wire 9 in the introducing tube 1, a partition member 12 is provided between the clip 3 and the manipulating wire 9. This partition member 12 is provided as an arc shaped member cutout from a plate material or tube. This partition member 12 may be inserted between the clip 3 and manipulating wire 9, or alternatively, may be securely bonded with the clip 3.

The partition member 12 is provided as a soft member made of silicon, Teflon, polyurethane, polyethylene, polypropylene, polyamide, Gore-Tex, rubber or the like, for example.

Preferably, a biocompatible material is desirable. In addition, the thickness of the partition member 12 is 1 mm or less, the length is 5 mm to 20 mm, and the width is about 3 mm or less.

Now, working of a fourth embodiment will be described here.

The introducing tube 1 of the clip apparatus is introduced into the body cavity via the channel of the endoscope inserted into the cavity. Then, the distal end portion of the introducing tube 1 is located at the clipping target tissue 6, for example, in close proximity to the gastric mucous membrane tissue. The compression member 11 is extruded in the distal end direction of the introducing tube 1, whereby the proximal end portion 3a of the clip 3 located at the most proximal end is extruded by the compression member 11. Then, a force is conveyed from the distal end of the clip 3 to the clip 3 at the distal end side, and the first clip 3 located at the most distal end is protruded from the distal end portion of the distal end clip 2.

At the clip 3, the opening/expanding properties are imparted to the arm sections 3b and 3b' so as to open the pinch sections 3c and 3c'. Thus, the clip 3 is protruded from the distal end tip 2, and at the same time, the pinch sections 3c and 3c' open.

While the pinch sections 3c and 3c' are pushed against the target tissue 6, when two manipulating wires 9 exposed from the proximal end of the introducing tube 1 are retracted, the ligating wire 10 can freely move on the manipulating wire 9. Thus, a loop of the ligating wire 10 is hooked on a return portion of the manipulating wire 9 at the distal end of the introducing tube 1, and the clip 3 located at the most distal end is retracted. Then, the clip arm sections 3b and 3b' bent in the expanding/opening direction are engaged with the distal end portion of the distal end tip 2.

When the manipulating wire 9 is further retracted, the projections 3f and 3f' provided at the clip arm sections 3b and 3b' are engaged with the distal end tip 2, and the traction force is applied onto to the clip 3. Then, the distal end portion 3a of the clip 3 is plastically deformed, and the pinch sections 3c and 3c' close, whereby the target tissue 6 can be pinched.

When the manipulating wire 9 is further retracted, the ligating wire 10 breaks, and the manipulating wire 9 and clip 3 are completely separated from each other. In this manner, legation of the first clip 3 located at the most distal end completes. At this time, at the clip 3 other than that located a the most distal end in the introducing tube 1, the partition member 12 is inserted between the clip 3 and the manipulating wire 9, thereby preventing a hitch between the manipulating wire 9 and the clip arm sections 3b and 3b'. The second or later clip 3 can be ligated in the same manner as in the first clip.

According to the fourth embodiment, in addition to the advantageous effect of the third embodiment, an interference between the manipulating wire and clip arm section does not occur. Thus, there is advantageous effect that the traction force quantity of the manipulating wire is reduced, thus making it possible to prevent a hitch between the manipulating wire and clip arm section.

FIG. 11 and FIG. 12 each show a fifth embodiment. Like constituent elements in the third embodiment are designated by like reference numerals. A duplicate description is omitted here.

In order to prevent a hitch between the clip arm sections 3b and 3b' and the manipulating wire 9 in the introducing tube 1, there is provided a tube shaped restricting member 13 externally engaged with the arm sections 3b and 3b' of the clip 3.

This restricting member 13 is made of a soft material such as silicon or rubber, for example. Preferably, a biocompatible material is desired. In addition, it is desirable that perforation 13a be provided so as to be easily torn so that the clip 3 expands and opens during legation of the clip 3. Further, the thickness of the restricting member 13 is about 0.3 mm or less. Preferably, it is desirable that the restricting member is small in thickness, and is easily torn.

Now, working of a fifth embodiment will be described here.

The introducing tube 1 of the clipping apparatus is inserted into the body cavity via the channel of the endoscope inserted into the cavity. Then, the distal end portion of the introducing tube 1 is located at the clipping target tissue 6, for example, in close proximity to the gastric mucous membrane tissue.

The compression member 11 is extruded in the distal end direction of the introducing tube 1, whereby the proximal end portion 3a of the clip 3 located at the most proximal end is extruded by the compression member 11. Then, a force is conveyed from the distal end portion of the clip 3 to the clip 3 at the distal end side, and the first clip 3 locate at the most distal end is protruded from the distal end portion of the distal end tip 2.

At the clip 3, the opening/expanding properties are imparted to the arm sections 3b and 3b' so as to open the pinch sections 3c and 3c'. Thus, the clip 3 is protruded from the distal end tip 2, and at the same time, the pinch sections 3a and 3c' open. While the pinch sections 3c and 3c' is pushed against the target tissue 6, when two manipulating wire 9 exposed from the proximal end of the introducing tube 1 are retracted, the ligating wire 10 can move arbitrary on the manipulating wire 9. Thus, a loop of the ligating wire 10 is hooked on a return portion of the manipulating wire 9 at the distal end of the introducing tube 1. Then, the clip 3 located at the most distal end is retracted, and the clip arm sections 3b and 3b' bent in the expanding/opening direction are engaged with the distal end portion of the distal end tip 2.

When the manipulating wire 9 is further retracted, the protrusions 3f and 3f' provided at the clip arm sections 3b and 3b' are engaged with the distal end tip 2. Then, the traction force is applied only to the clip 3, the proximal end portion 3a of the clip 3 is plastically deformed, and the pinch sections 3c and 3c' close, whereby the target tissue 6 can be pinched.

When the manipulating wire 9 is further retracted, the ligating wire 10 breaks and the manipulating wire 9 and clip 3 are completely separated from each other. At this time, the clip 3 other than that located at the most distal end in the introducing tube 1 prevents a hitch between the manipulating wire 9 and the clip arm sections 3b and 3b by means of the restricting member 13. In this manner, legation of the first clip 3 located at the most distal end completes.

Similarly, with respect to the second or later clip, the compression member 11 is extruded in the distal end direction of the introducing tube 1, whereby the clip 3 located at the most distal end is protruded from the distal end portion of the distal end tip 2. The clip 3 is protruded from the distal end tip 2, and at the same time, the restricting member 13 is torn by the opening/expanding properties of the clip 3, and the pinch sections 3a and 3c' open. The second or later clip can be ligated in the same manner as in the first clip.

According to the fifth embodiment, in addition to the advantageous effect of the third embodiment, the expansion of the clip arm sections is restricted in the introducing tube by means of the restricting member. Thus, a hitch between the internal face of the introducing tube and the clip arm section is reduced. Thus, there is an advantageous effect that the extrusion at the compression member 11 can be carried out with a smaller force when the clip is extruded in the distal end direction of the introducing tube.

FIG. 13A to FIG. 13C and FIG. 14 and FIG. 15 each show a sixth embodiment. In FIG. 13A, although five clips are configured, clips 14 may be mounted in series as long as a space in the introducing tube 1 is permitted. That is, if a sufficient space in the introducing tube 1 is provided, six and more clips 14 may be mounted.

At the clip 14 according to the present embodiment, a metallic thin band plate is bent at its center portion, and the bent portion is defined as a proximal end portion 14a. Then, both arms 14a and 14b' extending from this proximal end portion 14a are formed in the shape such that they are crossed each other. The proximal end portion 14a of the clip 14 is formed in a substantially oval shape. Further, the distal end rim portions of the arm sections 14a and 14b' of the clip 14 are bent so as to face to each other, and these portions are defined as pinch sections 14c and 14c'. One of the distal ends of the pinch sections 14c and 14c' is formed in a protrusive shape 14d' so as to easily pinch the living tissue, and the other is formed in a recess shape 14e. Then, the opening/expanding properties are imparted to the arm sections 14b and 14b' so as to open the pinch sections 14c and 14c'. As a material for the thin band plate of the clip 14, there are employed a stainless having resilience or an ultra-elastic alloy such as a nickel titanium alloy.

Further, a clip tightening ring 15 is engagingly fitted to the clip 14. The clip tightening ring 15 is molded of a resin and a metal having rigidity and elasticity. A pair of two blades 15*a* and 15*a*' that are elastically deformed and disposed to be arbitrarily protruded and recessed in the circumferential direction are provided at the outer periphery of the ring. The number of blades may be three or four without being limited to one or two. When an external force is applied to the circumferential face of the ring in the vertical direction, the blades 15*a* and 15*a*' are folded on the internal face of the clip tightening ring 15. The blades 15*a* and 15*a*' come into contact with the internal face of the distal end tip 2, and inclined faces 15*b* and 15*b*' are provided at their distal end sides. Thus, these blades can be extruded from the introducing tube 1 and distal end tip 2 smoothly and without resistance.

The clip tightening ring 15 is engagingly fitted to the clip arm sections 14*b* and 14*b*', whereby the clip arm sections 14*b* and 14*b*' are opened, and these arm sections are formed in a substantially tubular shape. The clip 14 and manipulating wire 9 are engaged with each other by routing the legation wire 10 through the clip proximal end portion 14*a*.

The blades 15*a* and 15*a*' of the clip tightening ring 15 may be mounted in the introducing tube 1 while these blades are folded. When the blades 15*a* and 15*a*' are mounted in the introducing tube 1 while they are protruded, elasticity of the blades 15*a* and 15*a*' can be maintained over a long period of time. In addition, a contact resistance between the inner face of the introducing tube 1 and the blades 15*a* and 15*a*' each is reduced. Thus, the force quantity can be reduced when the clip 14 is moved in the introducing tube 1.

The clip tightening ring 15 injection-molds a resin having rigidity and elasticity (polybutytelephthalate, polyamide, polyphenyl amide, liquid crystal polymer, polyether katone, or polyphthalic amide). Alternatively, an elastic metal (such as stainless or ultra-elastic alloy such as nickel titanium alloy) is molded by injection molding, grinding processing, plastic processing.

A tubular portion of this clip tightening ring 15 is about 0.6 mm to 1.3 mm in inner diameter, and is about 1.0 m to 2.1 mm in outer diameter. The outer most diameter portion when the blades 15*a* and 15*a*' are protruded is defined as 1 mm or more in diameter in consideration of engagement with the distal end tip 2.

Now, working of a sixth embodiment will be described here.

The introducing tube 1 of the clipping apparatus is introduced into the body cavity via the channel of the endoscope inserted into the cavity. Then, the distal end portion of the introducing tube 1 is located at the clipping target tissue 6, for example, in close proximity to the gastric mucous membrane tissue. The compression member 11 is extruded in the distal end direction of the introducing tube 1, whereby the proximal end portion of the clip tightening ring 15 located at the most proximal end is extruded by means of the compression member 11. Then, a force is conveyed from the clip tightening ring 15 to the clip 14 located at the most proximal end. Further, the force is conveyed from the distal end portion of the clip 14 to the clip tightening ring 15 at the distal end side, and the first clip 14 and clip tightening ring 15 located at the most distal end is protruded from the distal end portion of the distal end tip 2.

The blades 15*a* and 15*a*' of the clip tightening ring 15 are folded when they pass through the inside of the distal end tip 2. When the blades pass through the distal end tip 2, the blades 15*a* and 15*a*' are protruded again. In this manner, the clip tightening ring 15 is prevented from entering the inside of the distal end tip 2 again.

While the pinch portions 14*a* and 14*a*' of the clip 14 are pushed against the target tissue 6, when two manipulating wires 9 exposed from the proximal end of the introducing tube 1 are retracted, the legation wire 10 can freely move on the manipulating wire 9. Thus, a loop of the legation wire 10 is hooked on a return portion of the manipulating wire 9 at the most distal end of the introducing tube 1 and the clip 14 located at the most distal end is retracted. Then, the blades 15*a* and 15*a*' of the clip tightening ring 15 are engaged with the distal end portion of the distal end tip 2.

When the manipulating wire 9 is further retracted, an oval section of the proximal end portion 14*a* of the clip 14 is introduced into the clip tightening ring 15. Here, the dimensions of the oval section are larger than the inner diameter of the clip tightening ring 15, and thus, the oval section is crushed by the clip tightening ring 15. Then, the clip arm sections 14*b* and 14*b*' open significantly in outward direction.

In this state, the clip 14 is guided so as to pinch the target living tissue. Further, by retracting the manipulating wire 9, the arm sections 14*a* and 14*b*' of the clip 14 are introduced into the clip tightening ring 15, and the pinch sections 14*c* and 14*c*' of the clip 14 are closed. While the living tissue 6 is sandwiched between the clip arm sections 14*b* and 14*b*', the manipulating wire 9 is further retracted. Then, the ligating wire 10 breaks, and engagement between the manipulating wire 9 and clip 14 is released. In this manner, the first clip 14 located at the most distal end can be retained in the body cavity while the living tissue 6 is clipped. The second or later clip can be ligated in the same manner as in the first clip.

According to a sixth embodiment, in addition to the advantageous effect of the third embodiment, the clip arm section is closed by means of the clip tightening ring. Thus, there is an advantageous effect that a living tissue can be ligated with stronger force.

FIG. 16A to FIG. 16D each show a seventh embodiment. Like constituent elements in the third embodiment are designated by like reference numerals. A duplicate description is omitted here.

Figure 16A:
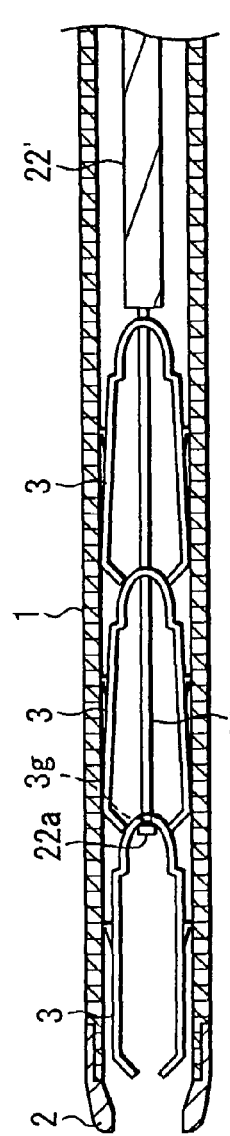
FIG. 16A to FIG. 16D are longitudinal side sections each showing a distal end portion of a clipping apparatus for explaining working of a seventh embodiment according to the present invention.

As shown in FIG. 16A, the distal end tip 2 whose inner diameter is gradually narrower toward the distal end portion is securely fixed to the distal end portion of the introducing tube 1. The manipulating wire 22 consists of an expansion portion 22*a* and a proximal end wire 22'. The proximal end wire 22' and manipulating wire 22 are welded or bonded with each other. Alternatively, when a core wire of the proximal end wire 22' composed of a twisted metal wire is used for the manipulating wire 22, only one wire will suffice. Thus, the number of parts is reduced, and the manufacturing cost can be reduced. The diameter of the proximal end wire 22' is about 0.3 mm to 1.5 mm.

A plurality of clips 3 are mounted in series at the distal end side of the introducing tube 1. These clips 3 are basically identical to those according to the first embodiment. A drilled hole 3*g* is provided at a bent portion of the proximal end portion 3*a*, and the manipulating wire 22 is inserted into this dripped hole 3*g*. An expansion portion 22*a* which is slightly larger than the dripped hole 3*g* is provided at the distal end portion of the manipulating wire 22. This expansion portion 22*a* is engaged with the proximal end portion 3*a* of the clip 3 at the most proximal end. In a state in which the clip 3 is mounted in the introducing tube 1, the pinch sections 3*c* and 3*c*' of the clip 3 abut against each other while the proximal end portion 3*a* of the immediately preceding clip 3 is pinched.

Now, working of a seventh embodiment will be described here.

Figure 16B:
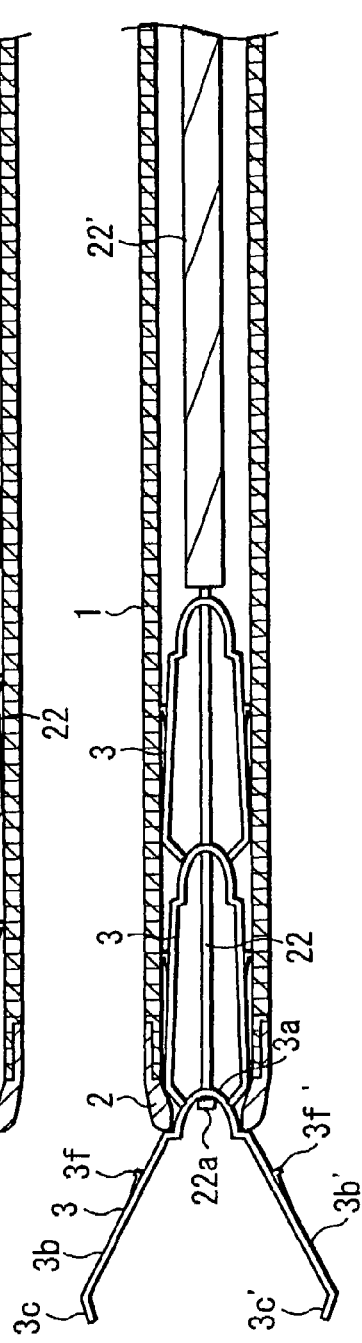
Figure 16C:
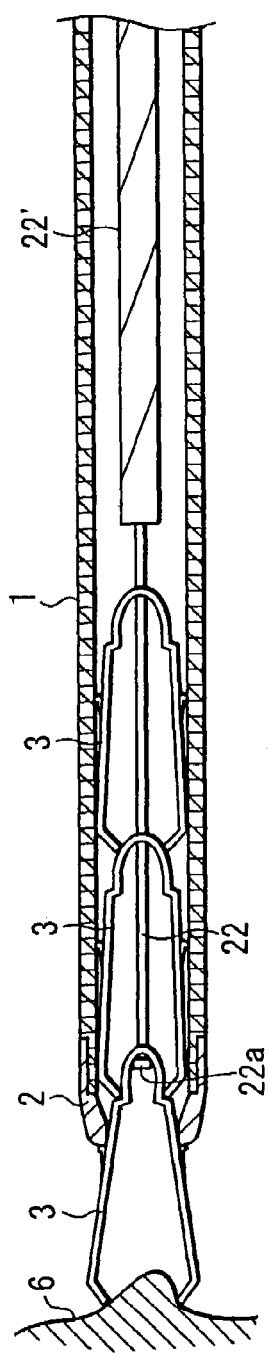

When the proximal end wire 22' is advanced or when the introducing tube 1 is retracted from the state shown in FIG. 16A, the clip 3 at the most distal end is advanced via the second and third clips 3. When the clip 3 is further pushed, the pinch sections 3c and 3c' of the second clip 3 clipping the first proximal end portion 3a abut against the internal wall of the distal end tip 2, as shown in FIG. 16B. Then, the second clip 3 is inhibited from being protruded from the distal end portion of the introducing tube 1. As shown in FIG. 16B, the arm sections 3b and 3b' of the clip 3 at the most frontal end significantly open. In this state, when the proximal end wire 22' is retracted, the projections 3f and 3f' provided at the arm sections 3b and 3b' of the clip 3 are engaged with the tip end portion of the distal end tip 2, as shown in FIG. 16C, and the traction force is applied only to the clip 3. When the proximal end wire 22' is further retracted, the proximal end portion 3a of the clip 3 is plastically deformed. Then, the pinch sections 3c and 3c' are closed, and the target tissue 6 can be pinched.

Figure 16D:
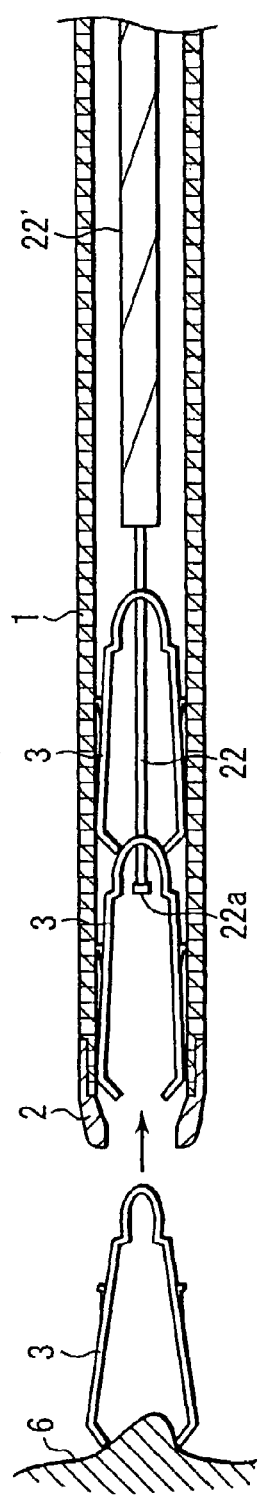

When the proximal end wire 22' is further retracted, as shown in FIG. 16D, a hole 3g of the proximal end portion 3a of the clip 3 is enlarged after deformed by the distal end expansion portion 22a of the manipulating wire 22, whereby the manipulating wire 22 can retain the clip 3 in a living tissue. The second or later clip 3 is manipulated in the same manner as in the first clip. In this manner, clips can be protruded and ligated by only one shot.

Therefore, there is no need to carry out careful protrusion manipulation, and operation can be simplified. In addition, when continuous legation is carried out, the surgical operation time can be reduced, and burdens on the patient and surgeon can be reduced. In addition, the number of parts is reduced, and the manufacturing cost can be reduced.

FIG. 17A to FIG. 17E, FIG. 18A, FIG. 18B, and FIG. 19 each show an eighth embodiment. Like constituent elements in the sixth embodiment are designated by like reference numerals. A duplicate description is omitted here.

As shown in FIG. 17A, three clips 14 shaped in the same manner as in the sixth embodiment and a clip tightening ring 29 as shown in FIG. 19 are alternately disposed in series each other in the introducing tube 1. The clip tightening ring 29 has the same structure as that according to the sixth embodiment, as shown in FIG. 15. That is, blades 30a and 30a' are provided as at least one pair of engaging means that is formed in the cylindrical shape made of a synthetic resin having elasticity or a metal and that is protruded in the circumferential direction at the distal end portion. At the distal ends of the blades 30a and 30a', downwardly inclined faces 30b and 30b' are formed toward the distal end of the clip tightening ring 29 in order to come into contact with the internal face of the distal end tip 2. In addition, a cylindrical short diameter portion 31a is provided at the distal end 31 of the clip tightening ring 29.

In addition, as shown in FIG. 17A to FIG. 17E, the clip 3 is connected to the manipulating wire 9 via the ligating wire 10. This ligating wire 10 is formed in a loop shape. This loop is routed into the manipulating wire 9 and the proximal end portion 3a of the clip 3, whereby the manipulating wire 9 and clip 3 are connected with each other. Further, the ligating wire can freely move on the manipulating wire 9 irrespective of the advancing/retracting movement of the manipulating wire 9.

In addition, as shown in FIG. 18A and FIG. 18B, a rod shaped manipulating section main body 24 is provided at the manipulating portion 23. The proximal end portion of the introducing tube 1 is fixed at the distal end portion of the manipulating section main body 24 by means of a fixing screw 25. The proximal end portion of the compression member 11 inserted into the introducing tube 1 is inserted into the internal cavity of the manipulating section main body 24, and is connected with a first slider 26 movably engaged with the manipulating section main body 24. Further, the proximal end portion of the manipulating wire 9 inserted into the compression member 11 is extended to the proximal end side of the manipulating section main body 24, and is connected with a second slider 27 movably engaged with the manipulating section main body 24. In addition, a finger hook ring 28 is provided at the proximal end portion of the manipulating section main body 24.

Therefore, the compression member 11 is advanced by manipulating the first slider 26, whereby the clip 3 can be protruded, and ligating manipulation of the clip 14 can be carried out via the manipulating wire 9 by manipulating the second slider 27.

Now, working of an eighth embodiment will be described here.

The introducing tube 1 of the clipping apparatus is introduced into the body cavity via the channel of the endoscope inserted into the cavity. Then, the distal end portion of the introducing tube 1 is located in close proximity to the clipping target tissue 6. When the compression member 11 is extruded in the distal end direction of the introducing tube 1 by manipulating the first slider 26 from the state shown in FIG. 17A, the first clip 14 located at the most distal end connected to the manipulating wire 9 and the clip tightening ring 29 are protruded from the distal end portion of the distal end tip 2, as shown in FIG. 17B.

The blades 30a and 30a' of the clip tightening ring 29 are folded when they pass through the inside of the distal end tip 2. When they pass through the distal end tip 2, the blades 30a and 30a' are protruded again.

As shown in FIG. 17C, when the manipulating wire 9 is retracted backwardly by manipulating the second slider 27, the proximal end portion 31 of the clip tightening ring 29 is introduced from the distal end tip 2 into the introducing tube 1. However, the blades 30a and 30a' abut against the distal end tip 2, and prevent the clip tightening ring 29 from entering the introducing 1 again. When the manipulating wire 9 is further retracted backwardly, the proximal end portion 14a of the clip 14 is introduced into the clip tightening ring 29 via he legation wire 10, and the pinch portions 14c and 14c' of the clip 14 open.

In this state, while the pinch portions 14a and 14a' of the clip 14 are pushed against the target tissue 6, when the manipulating wire 9 is further retracted, the arm sections 14b and 14b' of the clip 14 are introduced into the clip tightening ring 29, and the pinch portions 14c and 14c' of the clip 14 are closed. While the target tissue 6 is pinched by the pinch sections 14c and 14c' of the clip 14, when the manipulating wire 9 is further retracted, the legation wire 10 is broken, as shown in FIG. 17D. Therefore, the clip 14 and manipulating wire 9 containing the clip tightening ring 29 are separated from each other.

In this legation work, as shown in FIG. 17B, the pinch sections 14c and 14c' of the clip 14 pinch a short diameter portion 31a at the proximal end portion 31 of the clip tightening ring 20 connected to the second clip 14, and the second clip 14 can be inhibited from being protruded from the distal end portion of the introducing tube 1. The second or later clip 14 can be ligated in the same way as when the first clip is manipulated.

According to the present embodiment, the clip 14 can reliably receive a force applied by means of the manipulating wire 9 by using engaging means. Thus, the living tissue can be ligated with a stronger force. In addition, the arm sections 14b and 14b' of the clip 14 can be closed by means of the clip tightening ring 29, and thus, the living tissue can be ligated with a further stronger force.

In addition, the pinch sections 14c and 14c' of the clip 14 pinch the clip tightening ring 29, whereby the pinch sections 14c and 14c' of the clip 14 bump against the distal end tip 2. Then, only the clip 14 and clip tightening ring 29 located at the most distal end can be reliably protruded.

Further, the short diameter portion 31a of the proximal end portion 31 of the clip tightening ring 29 is formed in a cylindrical shape. Thus, there is an advantageous effect that an area which the pinch sections 14c and 14c' of the clip 14 pinch is increased, which is easily pinched.

The shape of the clip tightening ring 29 is not limited to the present embodiment, and the proximal end portion 31 may be formed in a conical shape, as shown in FIG. 20. When the proximal end portion is thus formed, even if the pinch sections 14c and 14c' of the clip 14 temporarily slips off from the proximal end portion 31 of the clip tightening ring 29, since the proximal end portion 31 is formed in a conical shape, the pinch sections 14c and 14c' of the clip 14 can pinch the proximal end portion 31 of the clip tightening ring 29 naturally by pressing the compression member 11. In addition, during assembling, there is no need to intentionally pinch the proximal end portion 31 of the clip tightening ring 29 at the pinch sections 14c and 14c' of the clip 14. Thus, assembling can be facilitated.

FIG. 21A to FIG. 21D each show a ninth embodiment. As shown in FIG. 21A, three clips 14 and the clip tightening ring 29 shaped in the same manner as in the eighth embodiment are alternately disposed in series at the introducing tube 1. However, the proximal end portion 31 of the clip tightening ring 29 according to the present embodiment does not have a short diameter portion 31a. According to the present embodiment, when the length of the manipulating wire 9 inserted into the introducing tube 1 is restricted, and the clip 14 and clip tightening ring 29 are protruded from the distal end portion of the introducing tube 1 by means of the compression member 11, the manipulating wire 9 is constructed so as to be protruded from the distal end portion of the introducing tube 1.

Now, working of a ninth embodiment will be described here.

The introducing tube 1 of the clipping apparatus is introduced into the body cavity via the channel of the endoscope inserted into the cavity. Then, the distal end portion of the introducing tube 1 is located in close proximity to the clipping target tissue 6. When the compression member 11 is extruded in the distal end direction of the introducing tube 1 from the state shown in FIG. 21A, the first clip 14 located at the most distal end connected with the manipulating wire 9 and the clip tightening ring 29 are protruded from the distal end portion of the distal end tip 2.

The blades 30a and 30a' of the clip tightening ring 29 are folded when they pass through the inside of the distal end tip 2. However, when they pass through the distal end tip 2, the blades 30a and 30a' are protruded again.

As shown in FIG. 21, when the manipulating wire 9 is retracted backwardly, the proximal end portion 31 of the clip tightening ring 29 is introduced from the distal end tip 2 into the introducing tube 1. The blades 30a and 30a' abut against the distal end tip 2, and prevent the clip tightening ring 29 from entering the introducing tube 1 again. When the manipulating wire 9 is further retracted backwardly, the proximal end portion 14a of the clip 14 is introduced into the clip tightening ring 29 via the ligating wire 10. Then, the pinch sections 14c and 14c' of the clip 14 open.

In this state, while the pinch sections 14a and 14a' of the clip 14 are pushed against the target tissue 6, when the manipulating wire 9 is further retracted, the arm sections 14 and 14b' of the clip 14 are introduced into the clip tightening ring 29. Then, the pinch sections 14c and 14c' of the clip 14 are closed. While the target tissue 6 is pinched by the pinch sections 14c and 14c', when the manipulating wire 9 is further retracted, the ligating wire 10 is broken, as shown in FIG. 21D. Therefore, the clip 14 including the clip tightening ring 29 and the manipulating wire 9 are separated from each other.

During this legation work, the length of the manipulating wire 9 is restricted so that the manipulating wire is not protruded from the distal end portion of the introducing tube 1. In addition, this length is defined such that the manipulating wire can be protruded from the distal end of the distal end tip 2 from the rear end of the blades 30a and 30a' of the first clip tightening ring 29 to the proximal end portion. Thus, the second clip 14 can be inhibited from being protruded from the tip end portion of the introducing tube 1. The second or later clip 14 can also be ligated in the same way as when the first clip is manipulated.

According to the present invention, the length of the manipulating wire 9 is merely restricted. Thus, a complicated structure is eliminated, and the number of parts is reduced. Therefore, the manufacturing cost can be reduced.

FIG. 22A to FIG. 22D each show a tenth embodiment.

Figure 22A:
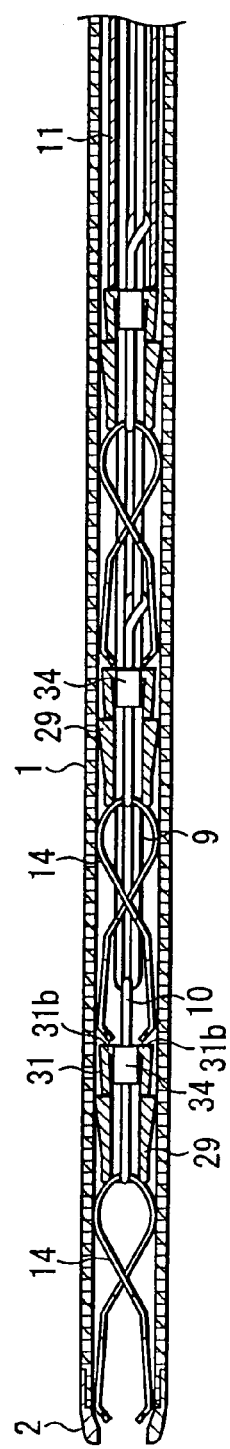
FIG. 22A to FIG. 22D are longitudinal side sections each showing a distal end portion of a clipping apparatus for explaining working of a tenth embodiment according to the present invention.
Figure 22B:
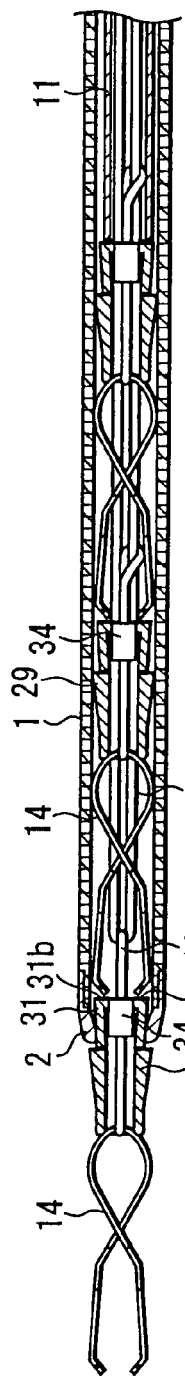

As shown in FIG. 22A, three clips 14 and clip tightening ring 29 shaped in the same manner as in the ninth embodiment are alternately disposed in series at the introducing tube 1. The proximal end portion 14a of the clip 14 is connected to the distal end portion of the manipulating wire 9 via the ligating wire 10.

A plurality of expansion pieces 31b that can be expanded/contracted in radial direction are provided at the proximal end portion 31 of the clip tightening ring 29. In addition, a cylindrically shaped extension member 34 is securely fixed to an immediate portion of the ligating wire 9. When this extension member 34 is pressed-in between the expansion pieces 31b of the clip tightening ring 29, and the expansion pieces 31b are expanded, the extension member is mounted on the introducing tube 1.

The extension member 34 is made of a metal or a resin having its rigidity, and is fixed with the ligating wire 10 by means of fusion welding, adhesive, or press-fit and the like. The external diameter of the extension member 34 is about 0.7 mm to 1.5 mm in diameter, and the length is 0.5 mm or more.

Now, working of a tenth embodiment will be described here.

The introducing tube 1 of the clipping apparatus is introduced into the cavity via the channel of the endoscope inserted into the cavity. Then, the distal end portion of the introducing tube 1 is located in close proximity to the clipping target tissue 6. The compression member 11 is pushed against the distal end direction of the introducing tube 1 from the state shown in FIG. 22A. At this time, a cylindrically shaped extension member 34 is securely fixed to an intermediate portion of the ligating wire 10. This extension member 34 is pressed-in between the expansion pieces 31b of the clip tightening ring 29, and the extension pieces 31b are extended. Thus, the extension pieces 31b abut against the internal face of the distal end tip 2. Then, the first clip 14 located at the most distant end connected to the manipulating wire 9 and the clip tightening ring 29 are protruded from a distal end portion of a distal end tip 2.

The blades 30a and 30a' of the clip tightening ring 29 are folded when they pass through the inside of the distal end tip 2. When the blades 30a and 30a' pass through the distal end tip 2, the blades are protruded again.

Figure 22C:
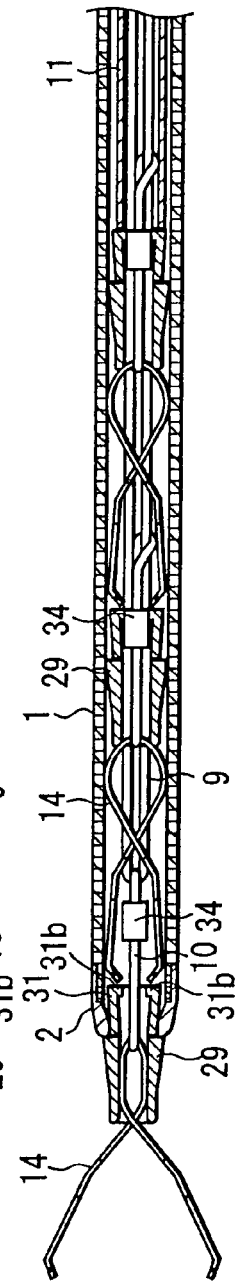

As shown in FIG. 22C, when the manipulating wire 9 is retracted backwardly, the proximal end portion 31 of the clip tightening ring 29 is introduced from the distal end tip 2 into the introducing tube 1. However, the blades 30a and 30a' abut against the distal end tip 2, and prevent the clip tightening ring 29 from entering the introducing tube 1 again. When the manipulating wire 9 is further retracted backwardly, the proximal end portion 14a of the clip 14 is introduced into the clip tightening ring 29 via the ligating wire 10. Then, the pinch sections 14c and 14c' of the clip 14 open. In addition, the extension member 34 slips off from the expansion piece 31b of the clip tightening ring 29, and the expansion piece 31b is contracted.

Figure 22D:
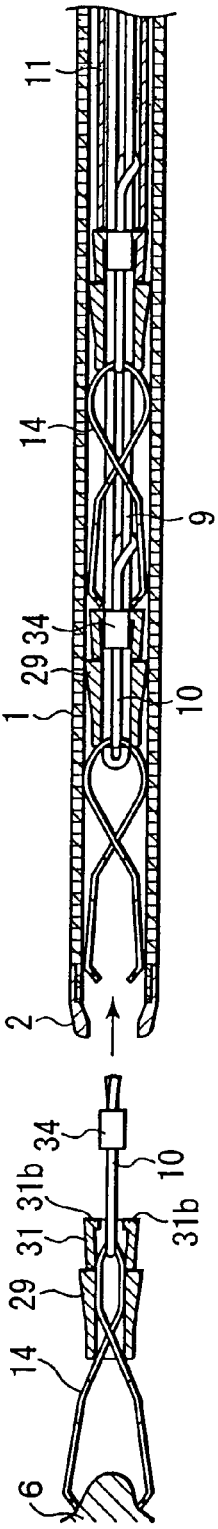

In this state, while the pinch sections 14a and 14a' of the clip 14 is pushed against the target tissue 6, when the manipulating wire 9 is further retracted, the arm sections 14b and 14b' of the clip 14 are introduced into the clip tightening ring 29. Then, the pinch sections 14c and 14c' of the clip 14 is closed. While the target tissue 6 is pinched by the pinch sections 14c and 14c', when the manipulating wire 9 is further retracted, the ligating wire 10 is broken, as shown in FIG. 22D. Therefore, the clip 14 including the clip tightening ring 29 and the manipulating wire 9 are separated from each other. The second or later clip 14 can be ligated in the same manner as when the first clip is manipulated.

According to the present embodiment, the clip tightening ring 29 abuts against the distal end tip 2 of the introducing tube 1 by means of the expansion member 34. Thus, only the clip 14 located at the most distal end and the clip tightening ring 29 can be protruded.

FIG. 23A to FIG. 23E each show an eleventh embodiment.

Figures 23A, 23B, 23C, 23D, 23E:
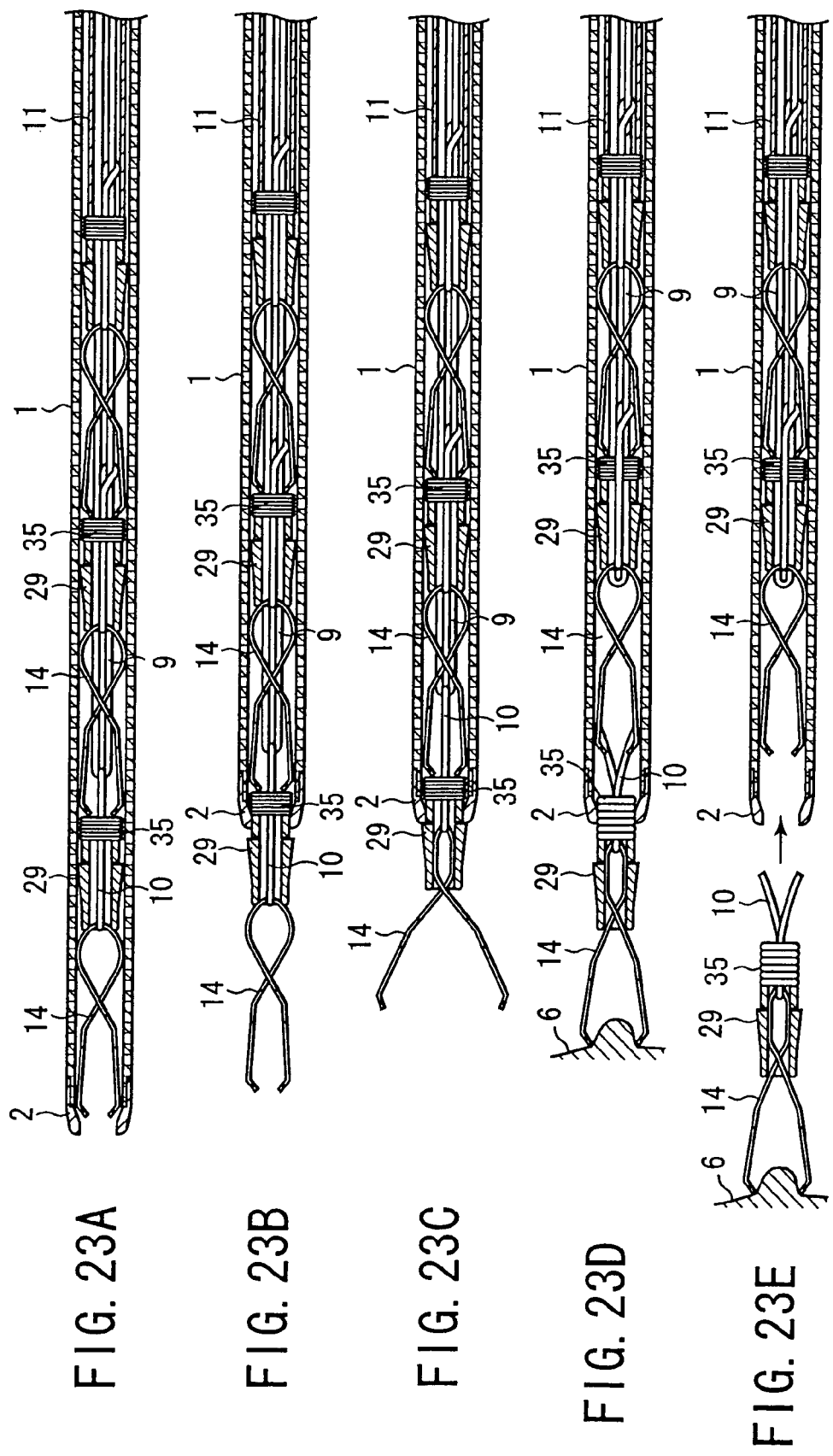
FIG. 23A to FIG. 23E are longitudinal side sections each showing a distal end portion of a clipping apparatus for explaining working of an eleventh embodiment according to the present invention.

As shown in FIG. 23A, three clips 14 shaped in the same manner as in the ninth embodiment and the clip tightening ring 29 are alternately disposed in series at the introducing tube 1. The proximal end portion 14a is connected to the distal end portion of the manipulating wire 9 via the ligating wire 10. At the proximal end portion 31 of the clip tightening ring 29, an expansion member 35 formed in a bellows shape, the outer diameter of which increases when the compression is applied and the outer diameter of which decreases when the compression force is released, is fixedly mounted on the introducing tube 1.

The bellows shaped expansion member 35 is made of a metal or a polymeric resin having resilience. The outer diameter increased when the compression force is applied is always greater than the inner diameter of the distal end of the distal end tip, which is about 1.1 mm to 3.5 mm in diameter. In addition, the expansion member 35 is securely fixed to the proximal end portion of the clip tightening ring 29 by means of fusion welding, adhesive, or press-fit and the like.

Now, working of an eleventh embodiment will be described here.

The introducing tube 1 of the clipping apparatus is introduced into the body cavity via the channel of the endoscope inserted into the cavity. Then, the distal end portion of the introducing tube 1 is located in close proximity to the target tissue 6. As shown in FIG. 23A, when the compression member 11 is extruded in the distal end direction of the introducing tube 1, the third clip 14 compresses the expansion member 35 of the clip tightening ring 29 of the second clip 14. Then, the second clip 14 compresses the expansion member 35 of the clip tightening ring 29 of the first clip 14. Thus, the expansion member 35 is compressed, and the external diameter increases.

Therefore, as shown in FIG. 23B, when the compression member 11 is extruded in the tip end direction of the introducing tube 1, the expansion member 35 is expanded. Thus, the expansion member 35 abuts against the internal face of the distal end tip 2. Then, the first clip 14 located at the most distal end connected to the manipulating wire 9 and the clip tightening ring 29 are protruded from the distal end portion of the distal end tip 2.

The blades 30a and 30a' of the clip tightening ring 29 are folded when they pass through the inside of the distal end tip 2. When the blades 30a and 30a' pass through the distal end tip 2, the blades are protruded again.

As shown in FIG. 23C, when the manipulating wire 9 is retracted backwardly, the proximal end portion 31 of the clip tightening ring 29 is introduced from the distal end tip 2 into the introducing tube 1. The blades 30a and 30a' abut against the distal end tip 2, and prevent the clip tightening ring 29 from entering the introducing tube 1. When the manipulating wire 9 is further retracted backwardly, the proximal end portion 14a of the clip 14 is introduced into the clip tightening ring 29 via the ligating wire 10. Then, the pinch sections 14c and 14c' of the clip 14 open.

In this state, while the pinch sections 14a and 14a' of the clip 14 are pushed against the target tissue 6, when the manipulating wire 9 is further retracted, the arm sections 14b and 14b' of the clip 14 are introduced into the clip tightening ring 29. Then, the pinch sections 14c and 14c' of the clip 14 are closed. While the target tissue 6 is pinched by the pinch sections 14c and 14c', when the manipulating wire 9 is further retracted, the ligating wire 10 is broken, as shown in FIG. 23D. Therefore, the expansion member 35 is spaced from the second clip 14. Thus, the compression force relevant to the expansion member 35 is released, and the expansion member 35 is decreased in outer diameter. Then, the expansion member 35 passes through the distal end tip 2, and the clip 14 including the clip tightening ring 29 and the manipulating wire 9 are separated from each other, as shown in FIG. 23E. The second or later clip 14 can be ligated in the same manner as when the first clip is manipulated.

According to the present embodiment, the clip tightening ring 29 abuts against the distal end tip 2 of the introducing tube 1 by means of the expansion member 35. Thus, only the clip 14 located at the distal end and the clip tightening ring 29 can be protruded.

FIG. 24A to FIG. 24D each show a twelfth embodiment.

Figure 24A:
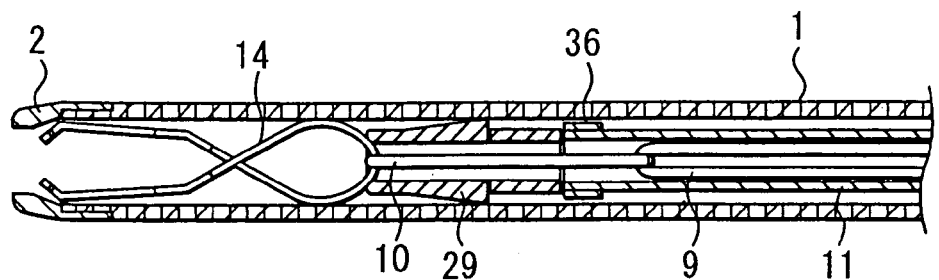
FIG. 24A to FIG. 24D are longitudinal side sections each showing a distal end portion of a clipping apparatus for explaining working of a twelfth embodiment according to the present invention.

FIG. 24A shows a state in which the last clip 14 and clip tightening ring 29 shaped in the same manner as in the ninth embodiment are disposed at the introducing tube 1. The proximal end portion 14a of the clip 14 is connected to the distal end portion of the manipulating wire 9 via the ligating wire 10. A stopper 36 consisting of a short tube is engagingly fitted to the distal end portion of the compression member 11, and the outer diameter of the distal end portion of the compression member 11 is greatly formed.

The stopper 36 is made of a metal or a polymeric resin and the like, and is reliably fixed at the distal end portion of the compression member 11 by means of fusion welding, adhesive, or press-fit and the like. The outer diameter of the stopper 36 is always larger than the inner diameter of the most distal end of the distal end tip, and is about 1.1 mm to 3.5 mm in diameter. In addition, when the length of the stopper 36 increases, the stopper becomes hard, thus making it impossible to extrude the clip 14 during angling. Thus, it is desirable that the stopper length is as short as possible.

Now, working of a twelfth embodiment will be described here.

Figure 24B:
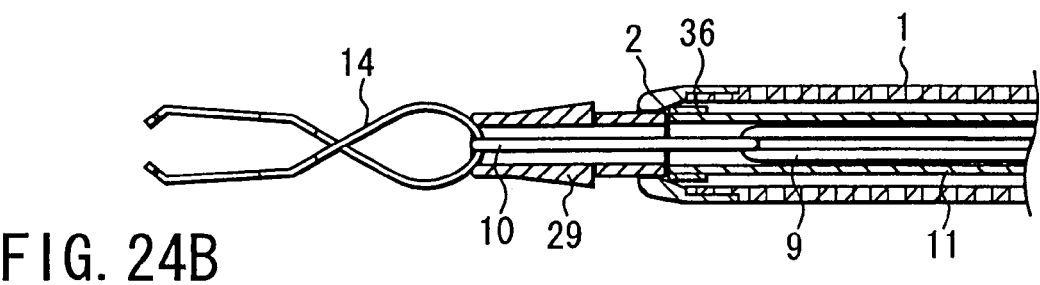

The introducing tube 1 of the clipping apparatus is introduced into the body cavity via the channel of the endoscope inserted into the cavity. Then, the distal end portion of the introducing tube 1 is located in close proximity to the clipping target tissue 6. As shown in FIG. 24A, when the compression member 11 is extruded in the distal end direction of the introducing tube 1, the last clip 14 and clip tightening ring 29 are protruded through the distal end tip 2 of the introducing tube 1, as shown in FIG. 24B. At this time, the stopper 36 at the distal end portion of the compression member 11 abuts against the internal face of the distal end tip 2, and the distal end portion of the compression member 11 is not protruded from the distal end portion of the introducing tube 1.

The blades 30a and 30a' of the clip tightening ring 29 are folded when they pass through the inside of the distal end tip 2. When they pass through the distal end tip 2, the blades 30a and 30a' are protruded again.

Figure 24C:
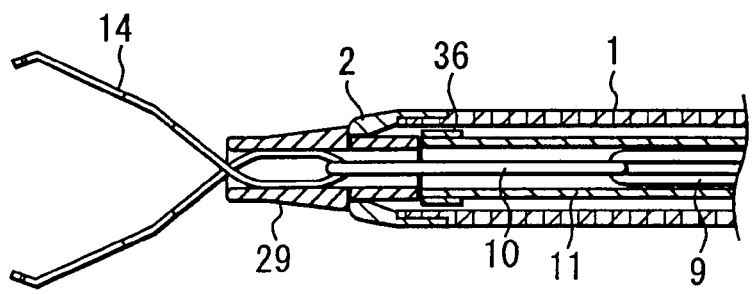

As shown in FIG. 24C, when the manipulating wire 9 is retracted backwardly, the proximal end portion 31 of the clip tightening ring 29 is introduced from the distal end tip 2 into the introducing tube 1. The blades 30a and 30a' abut against the distal end tip 2, and prevent the clip tightening ring 9 from entering the introducing tube 1 again. When the manipulating wire 9 is further retracted backwardly, the proximal end portion 14a of the clip 14 is introduced into the clip tightening ring 29 via the ligating wire 10. Then, the pinch sections 14c and 14c' of the clip 14 open.

Figure 24D:
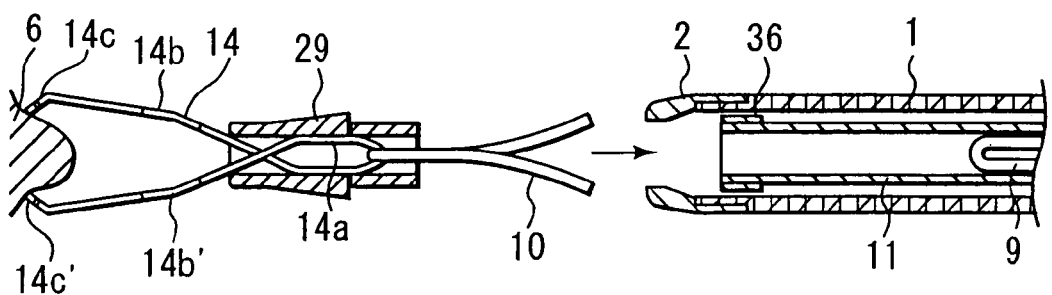

In this state, while the pinch sections 14a and 14a' of the clip 14 are pushed against the target tissue 6, when the manipulating wire 9 is further retracted, the arm sections 14b and 14b' of the clip 14 are introduced into the clip tightening ring 29. Then, the pinch sections 14c and 14c' of the clip 14 are closed. While the target tissue 6 is pinched by the pinch sections 14c and 14c', when the manipulating wire 9 is further retracted, the ligating wire 10 is broken, as shown in FIG. 24D. Therefore, the clip 14 including the clip tightening ring 29 and the manipulating wire 9 are separated from each other.

According to the present embodiment, the stopper 36 is provided at the distal end portion of the compression member 11. Thus, the distal end portion of the compression member 11 is not protruded from the distal end portion of the introducing tube 1, and only the last clip 14 and the clip tightening ring 29 can be protruded.

FIG. 25A to FIG. 25D each show a thirteenth embodiment.

Figure 25A:
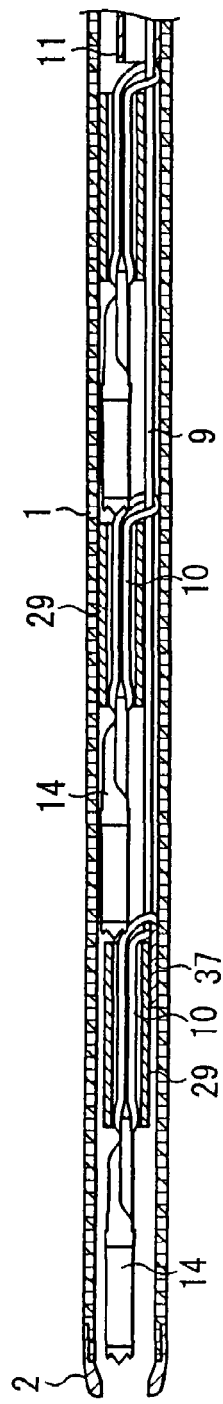
FIG. 25A to FIG. 25D are longitudinal side sections each showing a distal end portion of a clipping apparatus for explaining working of a thirteenth embodiment according to the present invention.

As shown in FIG. 25A, three clips 14 and a clip tightening ring 29 shaped in the same manner as in the ninth embodiment are alternately disposed in series at the introducing tube 1. A planar bonding member 37 abutting against the distal end tip 2 is connected to the distal end portion of the manipulating wire 9. The ligating wire 10 is engagingly inserted into the manipulating wire 9. During clip legation, this ligating wire 10 is engaged with the bonding member 37, or alternatively, is engaged with the distal end portion of the manipulating wire. The bonding member is made of a resin or a metal having rigidity, and is securely fixed at the distal end of the manipulating wire by means of fusion welding or adhesive. In addition, during wire breakage when the clip is ligated, it is desirable that the bonding member be of size that is free of interference during clip protrusion.

Now, working of a thirteenth embodiment will be described here.

Figure 25B:
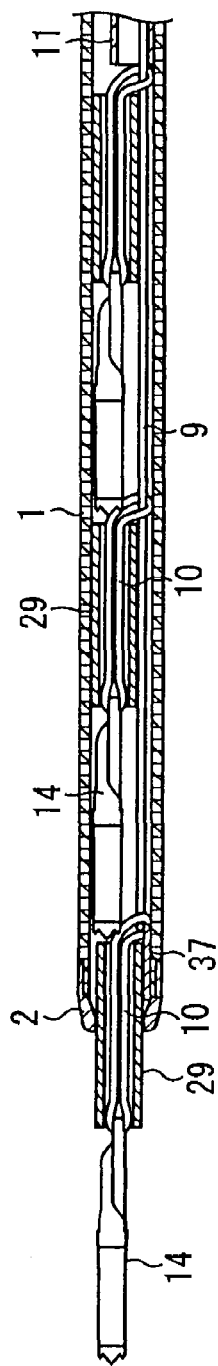

The introducing tube 1 of the clipping apparatus is introduced into the body cavity via the channel of the endoscope inserted into the cavity. The distal end portion of the introducing tube 1 is located in close proximity to the target tissue 6. As shown in FIG. 25A, when the compression member 11 is extruded in the distal end direction of the introducing tube 1, the bonding member 37 abuts against the internal face of the distal end tip 2 by the presence of the clip tightening ring 29 as shown in FIG. 25B. Then, the first clip 14 located at the most distal end connected to the manipulating wire 9 and the clip tightening ring 29 are protruded from the distal end portion of the distal end tip 2.

The blades 30a and 30a' of the clip tightening ring 29 are folded when they pass through the inside of the distal end tip 2. When the blades 30a and 30a' pass though the distal end tip 2, the blades are protruded again.

Figure 25C:
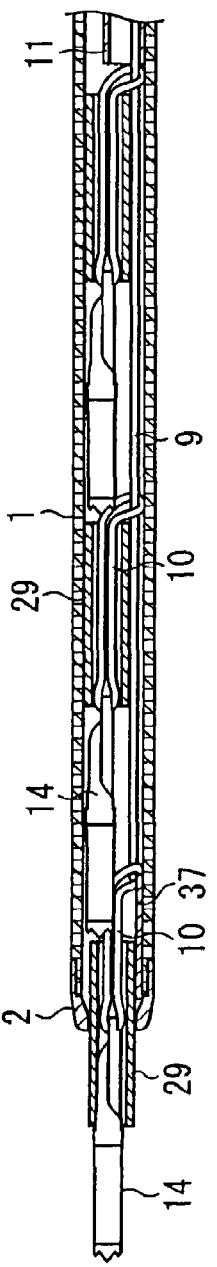

As shown in FIG. 25C, when the manipulating wire 9 is retracted backwardly, the proximal end portion 31 of the clip tightening ring 29 is introduced from the distal end tip 2 into the introducing tube 1. The blades 30a and 30a' abut against the distal end tip 2, and prevent the introducing tube 1 from entering the introducing tube 1 again. When the manipulating wire 9 is further retracted backwardly, the proximal end portion 14a of the clip 14 is introduced into the clip tightening ring 29 via the ligating wire 10. Then, the pinch sections 14c and 14c' of the clip 14 open.

Figure 25D:
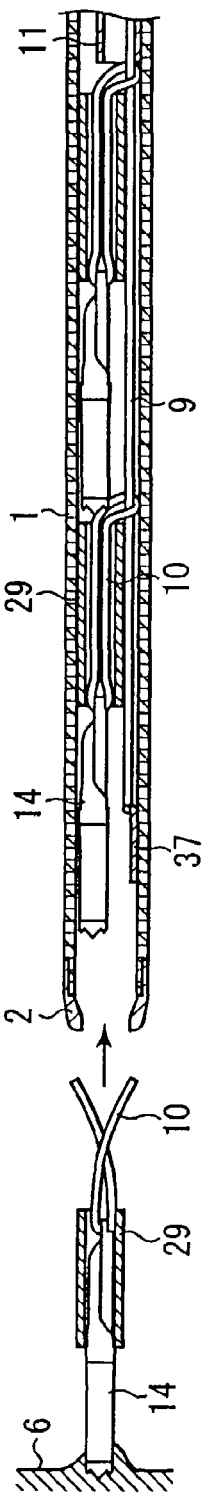

In this state, while the pinch sections 14a and 14a' of the clip 14 are pushed against the target tissue 6, when the manipulating wire 9 is further retracted, the arm sections 14b and 14b' of the clip 14 is introduced into the clip tightening ring 29'. Then, the pinch sections 14c and 14c' of the clip 14 are closed. While the target tissue 6 is pinched by the pinch sections 14c and 14c', when the manipulating wire 9 is further retracted, the ligating wire 10 is broken, as shown in FIG. 25D. Therefore, the clip 14 including the clip tightening ring 29 and the ligating wire 10 are separated from each other. The second or later clip 14 can be ligated in the same manner as when the first clip is manipulated.

According to the present embodiment, the bonding member 37 abuts against the distal end tip 2. Thus, only the clip 14 located at the most distal end and the clip tightening ring 29 can be protruded.

FIG. 26A to FIG. 26D each show a fourteenth embodiment.

As shown in FIG. 26A, three clips 14 and the clip tightening ring 29 shaped in the same manner as in the ninth embodiment are alternately disposed in series at the introducing tube 1. At the inside of the introducing tube 1, a guide wire 38 is provided with tension over its axial direction. The distal end portion of the guide wire 38 is connected to a post 39 protruded in close proximity to the distal end portion of the introducing tube 1.

The ligating wire 10 is connected to the proximal end portion 14a of the clip 14. This ligating wire 10 is movably inserted relevant to the guide wire 38. In addition, the ligating wire 10 is movably inserted relevant to the manipulating wire 9 returned in the same way. The post 39 is made of a metal or a resin, and is reliably fixed to the internal face of the distal end tip or the distal end portion of the introducing tube by means of fusion welding, adhesive, or press-fit and the like. The post 39 is of size that is free of interference during clip protrusion. It is desirable that the outer diameter be 1 mm or less, and the length be 1.5 mm or less. In addition, the guide wire 38 is made of a single metal wire or twisted wire, or alternatively, a polymeric fiber and the like, and the minimally small diameter is desirable. The guide wire 38 and post 39 are fixed to each other by means of fusion welding or adhesive.

Now, working of a fourteenth embodiment will be described here.

The introducing tube 1 of the clipping apparatus is introduced into the body cavity via the channel of the endoscope inserted into the cavity. The distal end portion of the introducing tube 1 is located in close proximity of the target tissue 6. As shown in FIG. 26A, when the compression member 11 is extruded in the distal end portion of the introducing tube 1, the first clip 14 located at the most distal end connected via the ligating wire 10 located at the distal end portion of the manipulating wire 9 and the clip tightening ring 29 are protruded, as shown in FIG. 26B. At this time, the loop portion of the ligating wire 10 is engagingly locked with the post 39 at the distal end portion of the guide wire 38, and the ligating wire 10 is not protruded from the distal end portion of the introducing tube 1.

The blades 30a and 30a' of the clip tightening ring 29 are folded when they pass through the inside of the distal end tip 2. When these blades 30a and 30a' pass through the distal end tip 2, the blades are protruded again.

As shown in FIG. 26C, when the manipulating wire 9 is retracted backwardly, the proximal end portion 31 of the clip tightening ring 29 is introduced from the distal end tip 2 into the introducing tube 1. The blades 30a and 30a' abut against the distal end tip 2, and prevents the clip tightening ring 29 from entering the introducing tube 1 again. When the operating wire 9 is further retracted backwardly, the proximal end portion 14a of the clip 14 is introduced into the clip tightening ring 29 via the ligating wire 10. Then, the pinch sections 14c and 14c' of the clip 14 open.

In this state, while the pinch sections 14a and 14a' of the clip 14 are pushed against the target tissue 6, when the manipulating wire 9 is further manipulated, the arm sections 14b and 14b' are introduced into the clip tightening ring 29. Then, the pinch sections 14c and 14c' of the clip 14 are closed. While the target tissue 6 is pinched by the pinch sections 14c and 14c', when the manipulating wire 9 is further retracted, the ligating wire 10 is broken, as shown in FIG. 26D. Therefore, the clip 14 including the clip tightening ring 29 and the manipulating wire 9 are separated from each other. The second or later clip 14 can be ligated in the same manner as when the first clip is manipulated.

According to the present embodiment, the ligating wire 10 is engagingly locked with the post 39 at the distal end portion of the guide wire 38. The ligating wire 10 is not protruded from the distal end portion of the introducing tube 1, and only the clip 14 located at the most distal end and the clip tightening ring 29 can be protruded. The second or later clip 14 can be ligated in the same way as when the first clip is manipulated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for ligating living tissues comprising:
an introducing tube capable of being inserted into a living body cavity;
a manipulating wire movably inserted into the introducing tube;
at least two clips; and
a connecting member which engages each of the clips and the manipulating wire with each other, wherein, in ligating the clips separately to a living tissue, a tensile stress of the manipulating wire is applied only to the clip located at a most distal end of the introducing tube;
wherein, said connecting member is a loop shaped wire formed between said manipulating wire and said clip.

2. An apparatus for ligating living tissues comprising:
an introducing tube capable of being inserted into a living body cavity;
a manipulating wire movably inserted into the introducing tube;
at least two clips;
a connecting member which engages each of the clips and the manipulating wire with each other, wherein, in ligating the clips separately to a living tissue, a tensile stress of the manipulating wire is applied only to the clip located at a most distal end of the introducing tube; and
a clip tightening ring engagingly mounted on arm sections of said clip, thereby closing pinch sections of said clip; and engaging means provided at least at one of said introducing tube and said clip tightening ring, which causes said introducing tube and said clip tightening ring to be engaged with each other when said clip and said clip tightening ring are protruded forwardly of said introducing tube, and inhibits said clip tightening ring from being stored in said introducing tube again.

3. An apparatus for ligating living tissues comprising:
an introducing tube capable of being inserted into a living body cavity;
a manipulating wire movably inserted into the introducing tube;
at least two clips; and
a connecting member which engages each of the clips and the manipulating wire with each other, wherein, in ligating the clips separately to a living tissue, a tensile stress of the manipulating wire is applied only to the clip located at a most distal end of the introducing tube;
wherein, when the tensile stress is applied between said clip positioned at the most distal end and said manipulating wire, said connecting member is configured to be deformed or broken more easily than said manipulating wire.

* * * * *